United States Patent [19]

Smith et al.

[11] Patent Number: 5,797,536
[45] Date of Patent: Aug. 25, 1998

[54] ENDOSCOPIC SURGICAL INSTRUMENT WITH PIVOTABLE AND ROTATABLE STAPLE CARTRIDGE

[75] Inventors: Jack Edward Smith, Dayton; James J. Bedi, Cincinnati; Thomas J. Sierocuk, Blue Ash; Thomas Howard Graves, Jr., Milford, all of Ohio

[73] Assignee: Ethicon, Inc., Somerville, N.J.

[21] Appl. No.: 413,654

[22] Filed: Mar. 30, 1995

Related U.S. Application Data

[60] Division of Ser. No. 80,462, Jun. 21, 1993, Pat. No. 5,431,323, which is a continuation-in-part of Ser. No. 959,184, Oct. 9, 1992, Pat. No. 5,381,943.

[51] Int. Cl.⁶ ............................................. A61B 17/068
[52] U.S. Cl. ....................... 227/175.1; 227/19; 227/177.1
[58] Field of Search ............................. 227/19, 175.1, 227/176.1, 177.1, 179.1

[56] References Cited

U.S. PATENT DOCUMENTS

| | | | |
|---|---|---|---|
| 2,507,710 | 5/1950 | Grosso | 128/312 |
| 3,593,903 | 7/1971 | Astafiev | 227/76 |
| 4,427,008 | 1/1984 | Transue | 128/325 |
| 4,506,819 | 3/1985 | Rand | 227/120 |
| 4,562,839 | 1/1986 | Blake, III et al. | 128/326 |
| 4,566,620 | 1/1986 | Green et al. | 228/19 |
| 4,573,622 | 3/1986 | Green et al. | 227/19 |
| 4,607,638 | 8/1986 | Crainich | 128/335 |
| 4,664,305 | 5/1987 | Blake, III et al. | 227/19 |
| 4,691,853 | 9/1987 | Storace | 227/19 |
| 4,706,668 | 11/1987 | Backer | 128/325 |
| 4,728,020 | 3/1988 | Green et al. | 227/198 |
| 4,754,909 | 7/1988 | Barker et al. | 227/19 |
| 4,807,628 | 2/1989 | Peters et al. | 227/176.1 |
| 4,869,414 | 9/1989 | Green et al. | 227/19 |

(List continued on next page.)

FOREIGN PATENT DOCUMENTS

| | | | |
|---|---|---|---|
| 0 116 220 A1 | 8/1984 | European Pat. Off. | A61B 17/12 |
| 0 484 677 A1 | 5/1992 | European Pat. Off. | A61B 17/072 |
| 0-541 987 | 5/1993 | European Pat. Off. | |
| 3301713 A1 | 7/1984 | Germany | A61B 17/11 |
| WO 88/01486 | 3/1988 | WIPO | |

*Primary Examiner*—Joseph J. Hail, III
*Assistant Examiner*—Jay A. Stelacone
*Attorney, Agent, or Firm*—Paul A. Coletti

[57] ABSTRACT

A surgical instrument is provided which is insertable through an endoscopic tube to enable a surgeon to perform a surgical technique inside a body cavity. The surgical instrument includes a shaft with a pivotally mounted tip attached thereto, the shaft extending from a handle for gripping the instrument for insertion to the body cavity. The tip of the shaft is adjustable to different angular orientations relative to the support shaft and is rotatable at any angular orientation of the tip. The support shaft may be rotatable about its longitudinal axis relative to the handle, or it may be fixed with respect to the handle, in which case the handle may be rotated to rotate the shaft inside the body cavity. In one embodiment, the surgical instrument comprises an endoscopic stapling device and the tip of the instrument comprises a staple cartridge which is rotatable 360° about its axes after the cartridge has been articulated with respect to the support shaft. An improved device for articulating the shaft tip is also provided in which a control knob is mounted to the support shaft for providing sweeping articulation of the shaft tip. Separate actuator mechanisms are provided on the handle to control the pivotal movement of the shaft tip, as well as the rotation of the shaft tip and the rotation of the support shaft.

8 Claims, 20 Drawing Sheets

U.S. PATENT DOCUMENTS

| | | | |
|---|---|---|---|
| 4,872,456 | 10/1989 | Hasson | 128/321 |
| 4,880,015 | 11/1989 | Nierman | 128/751 |
| 4,944,443 | 7/1990 | Oddsen et al. | 227/19 |
| 5,018,657 | 5/1991 | Pedlick et al. | 227/178 |
| 5,040,715 | 8/1991 | Green et al. | 227/176 |
| 5,042,707 | 8/1991 | Taheri | 606/213 |
| 5,084,057 | 1/1992 | Green et al. | 606/142 |
| 5,114,065 | 5/1992 | Storace | 227/175.1 |
| 5,125,553 | 6/1992 | Oddsen et al. | 227/175 |
| 5,147,373 | 9/1992 | Ferzli | 606/144 |
| 5,161,725 | 11/1992 | Murray et al. | 227/182 |
| 5,163,945 | 11/1992 | Ortiz et al. | 606/142 |
| 5,174,276 | 12/1992 | Crockard | 128/4 |
| 5,174,487 | 12/1992 | Rothfuss et al. | 227/176 |
| 5,176,702 | 1/1993 | Bales et al. | 606/208 |
| 5,222,975 | 6/1993 | Crainich | 606/219 |
| 5,240,163 | 8/1993 | Stein et al. | 227/175 |
| 5,251,801 | 10/1993 | Ruckdeschel et al. | 227/177.1 |
| 5,258,010 | 11/1993 | Green et al. | 227/176.1 |
| 5,289,963 | 3/1994 | McGarry et al. | 227/175 |
| 5,312,023 | 5/1994 | Green et al. | 227/175 |
| 5,326,013 | 7/1994 | Green et al. | 227/176 |
| 5,356,064 | 10/1994 | Green et al. | 227/177 |
| 5,478,003 | 12/1995 | Green et al. | 227/176.1 |

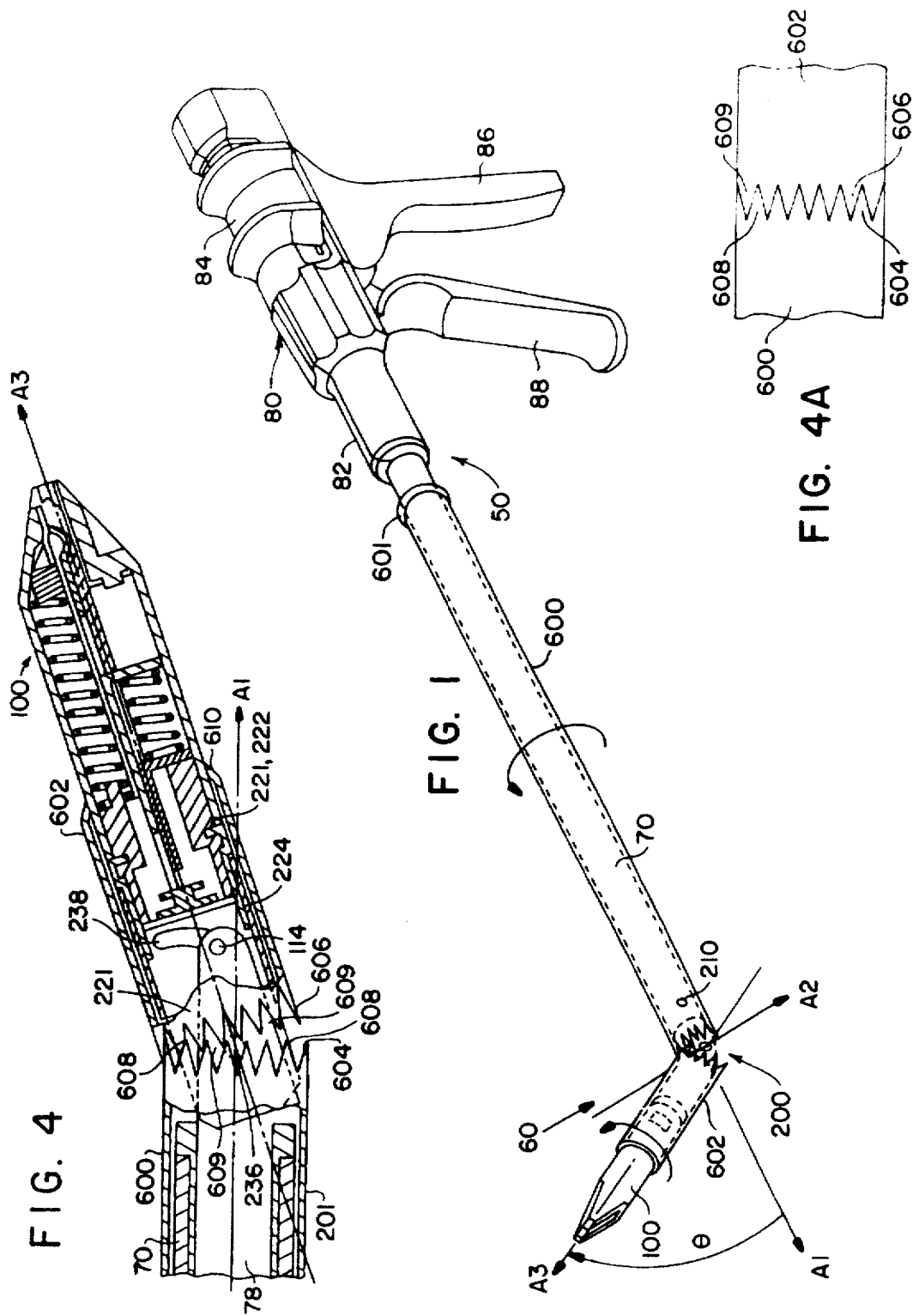

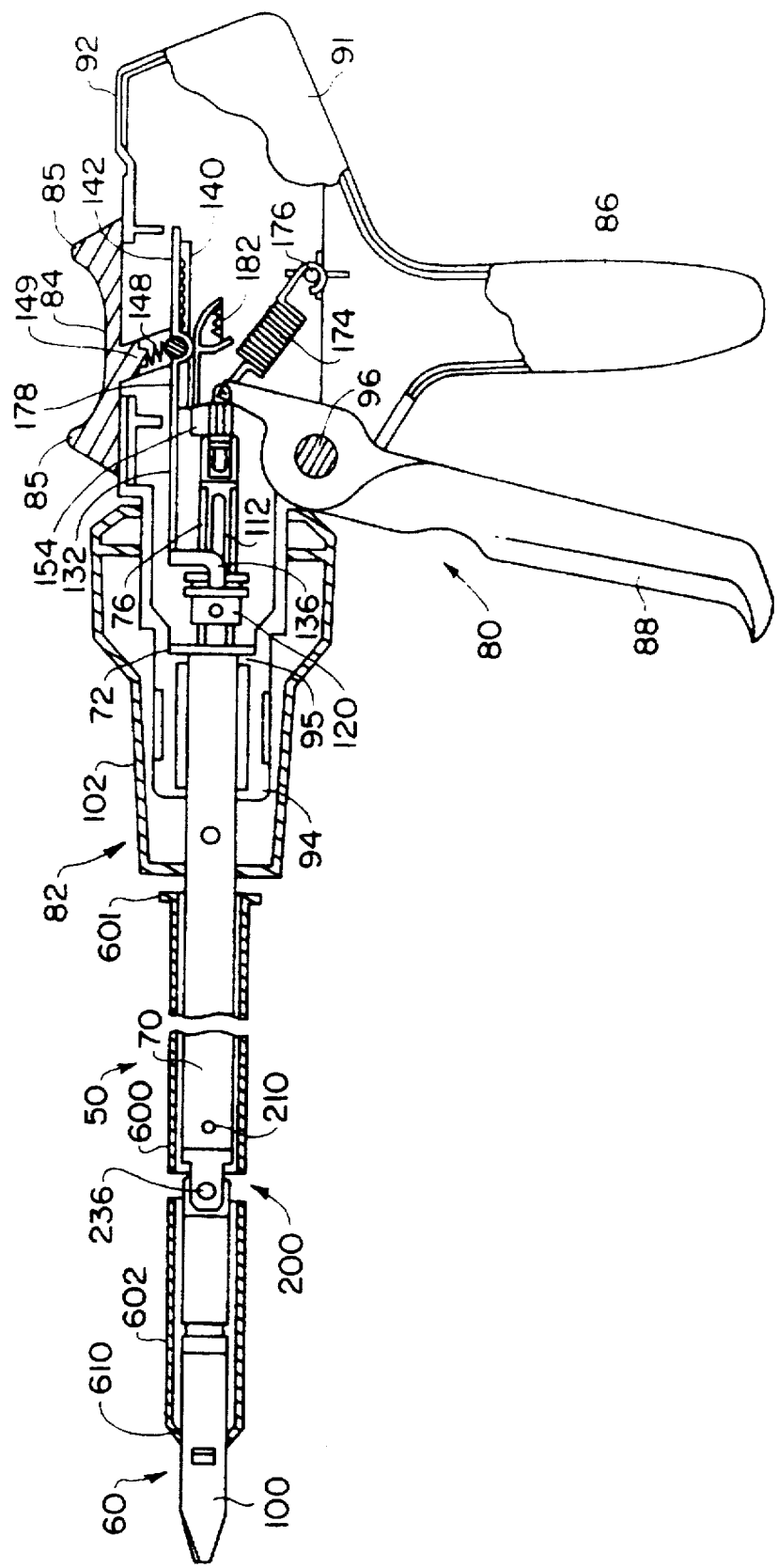

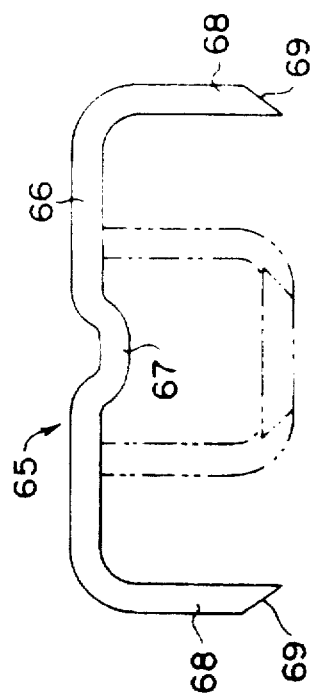
FIG. 17
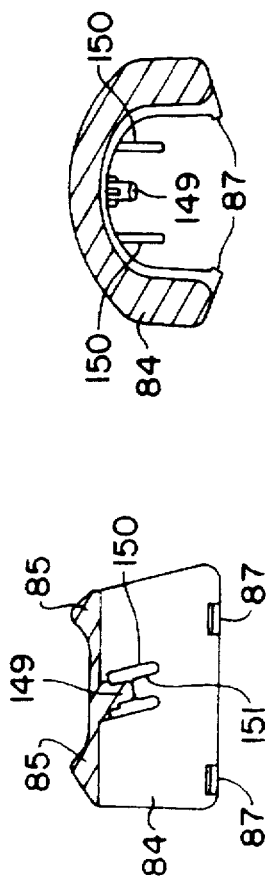
FIG. 16
FIG. 15
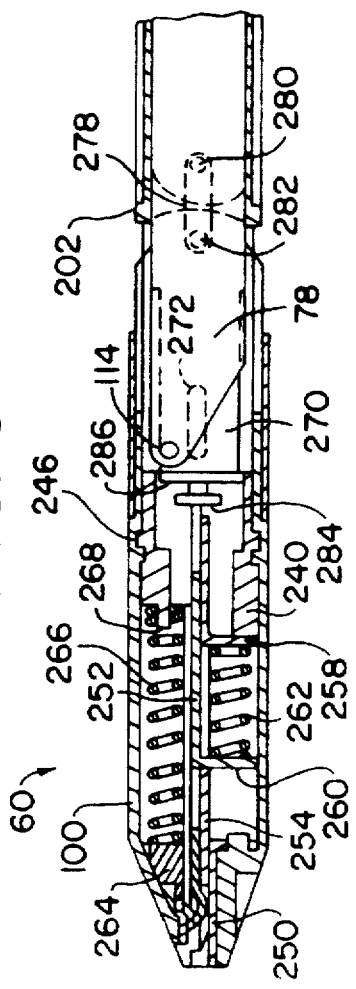
FIG. 3

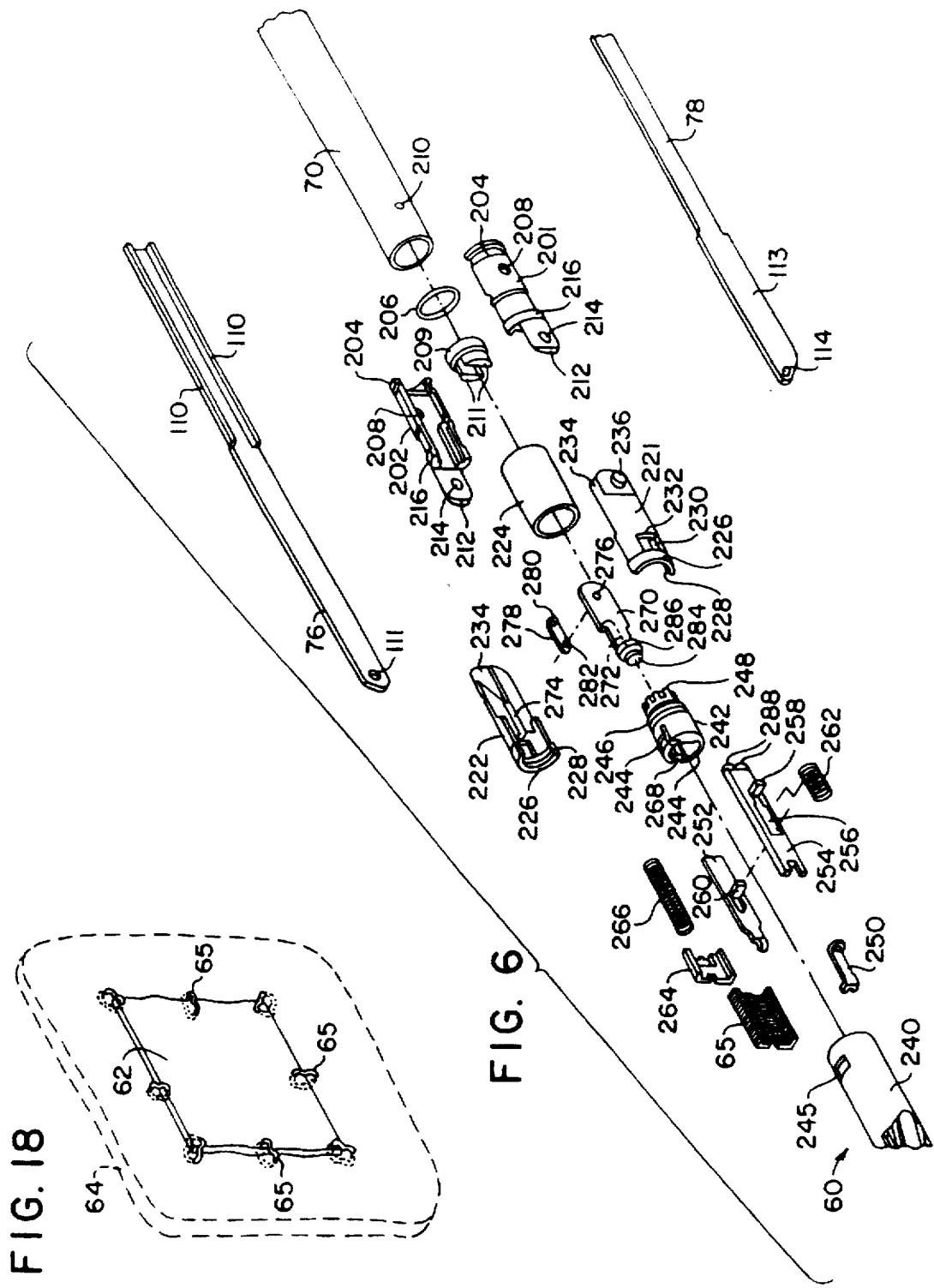

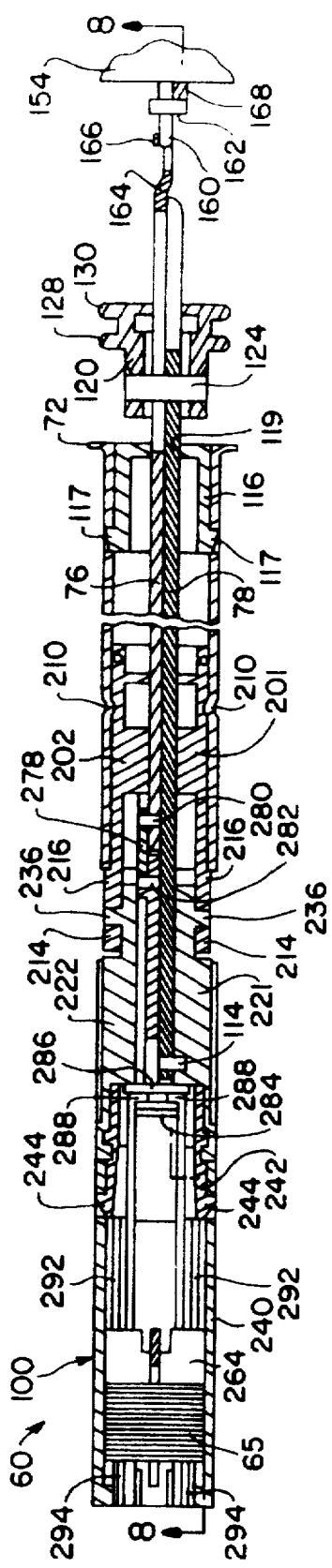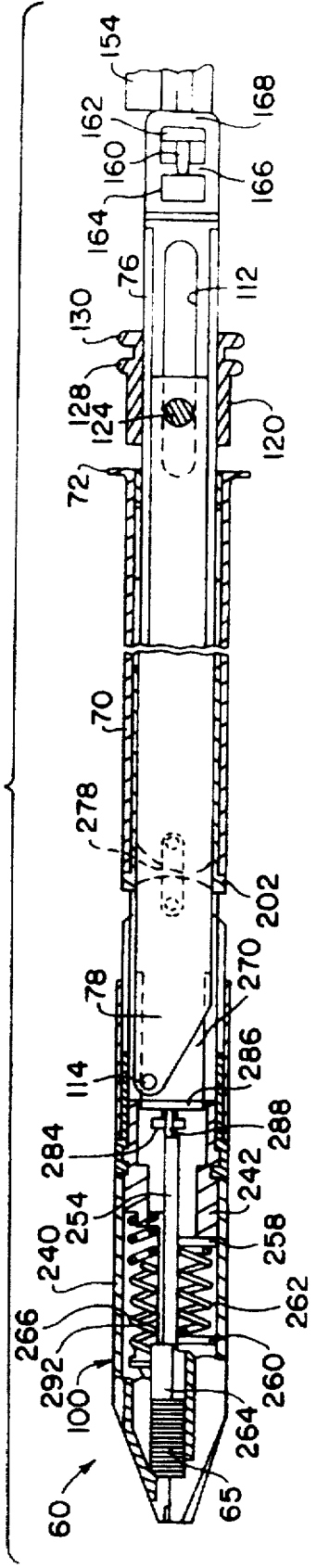

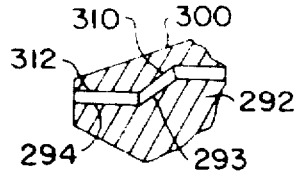
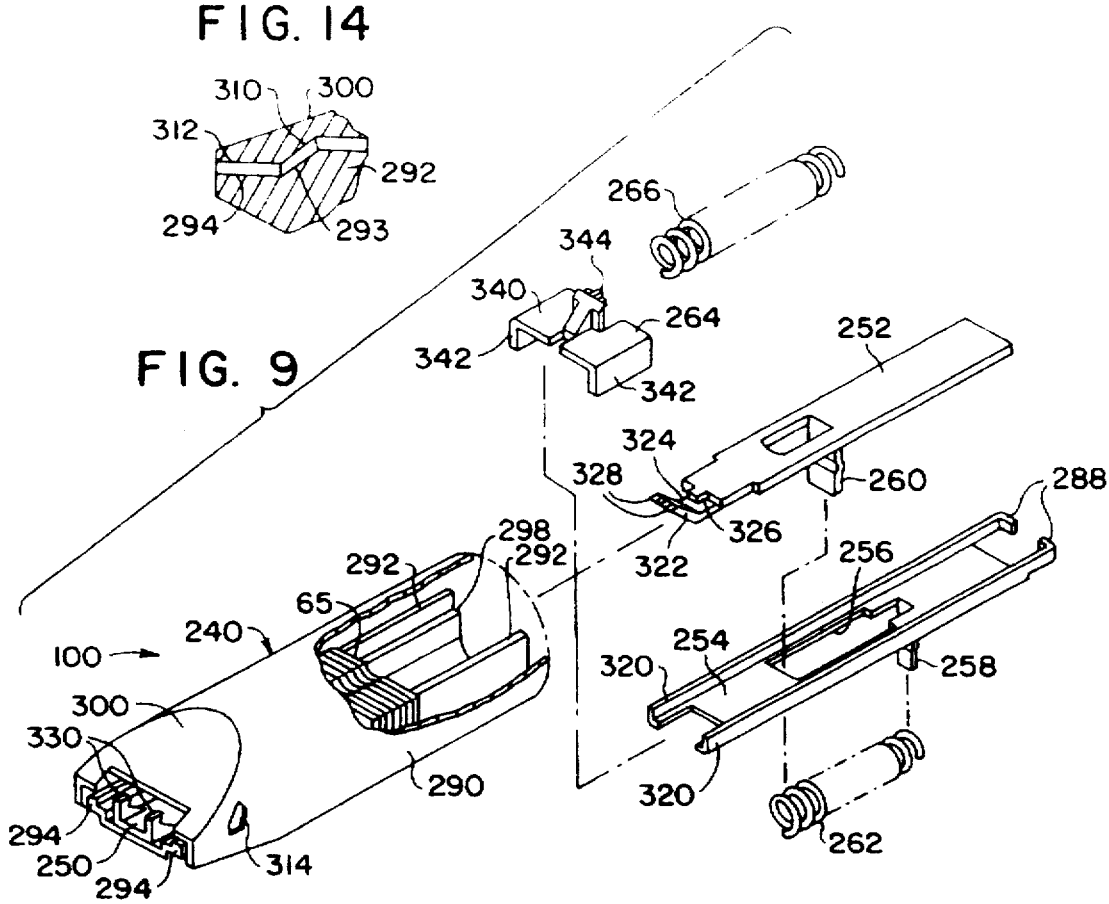
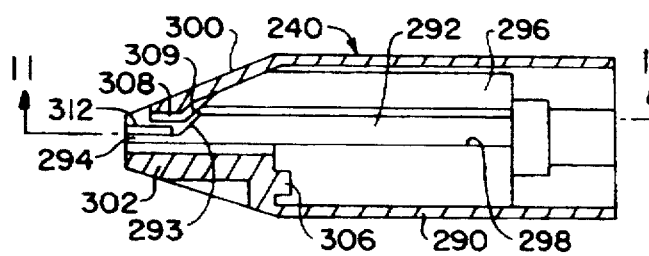
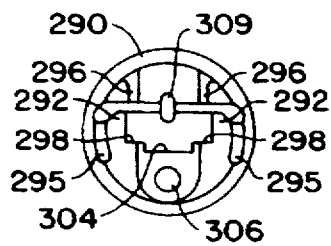
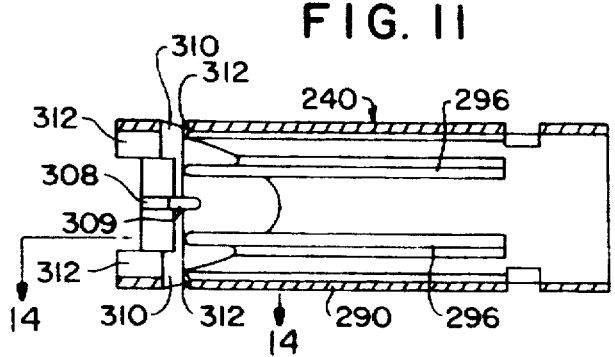
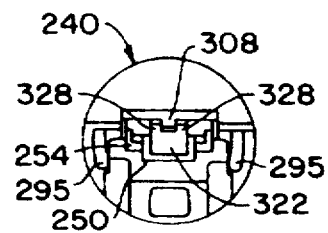

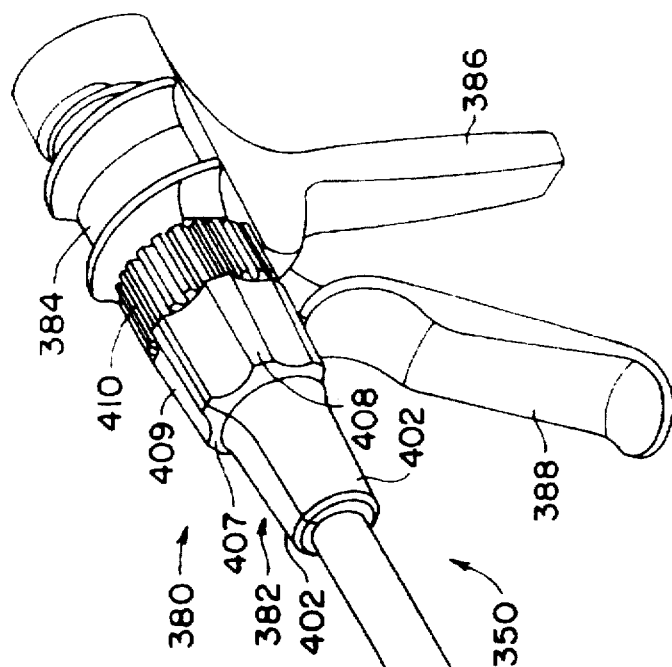
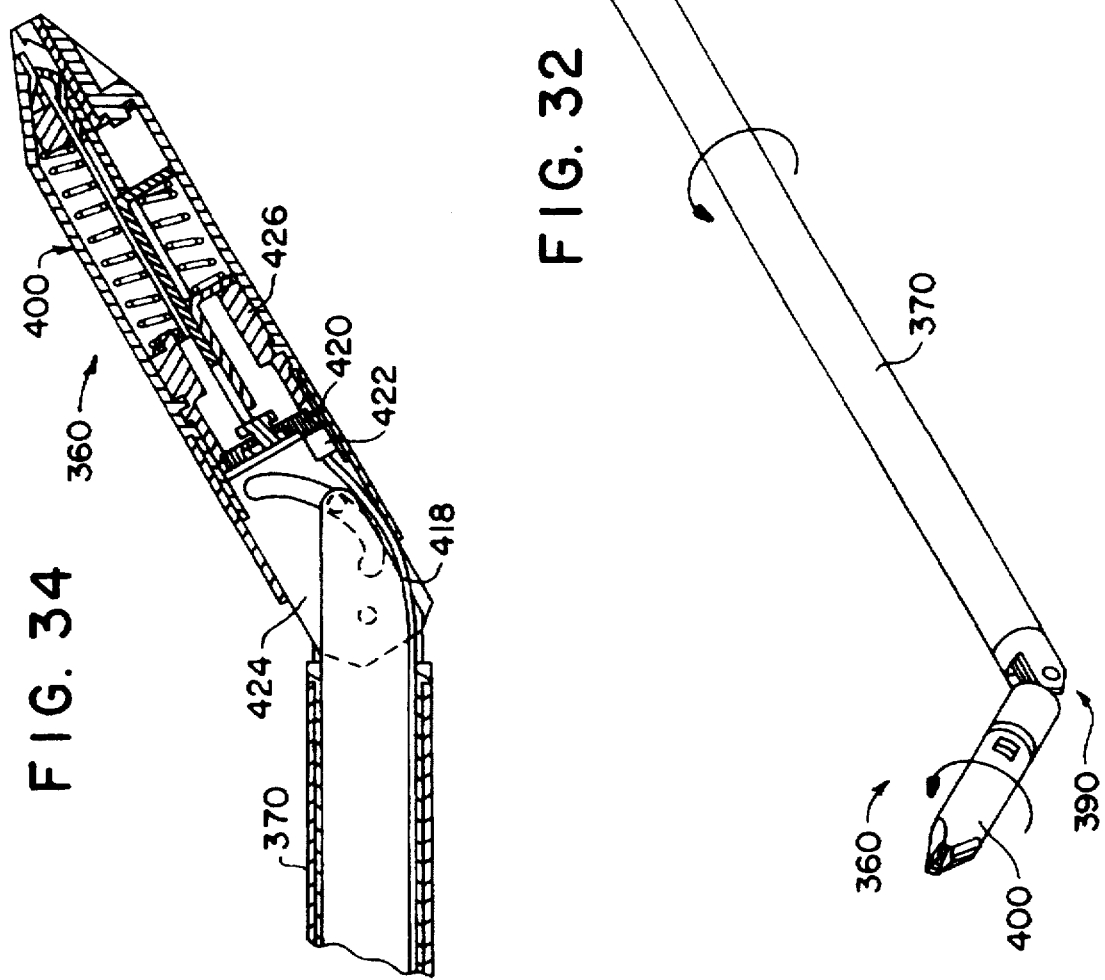
FIG. 32
FIG. 34

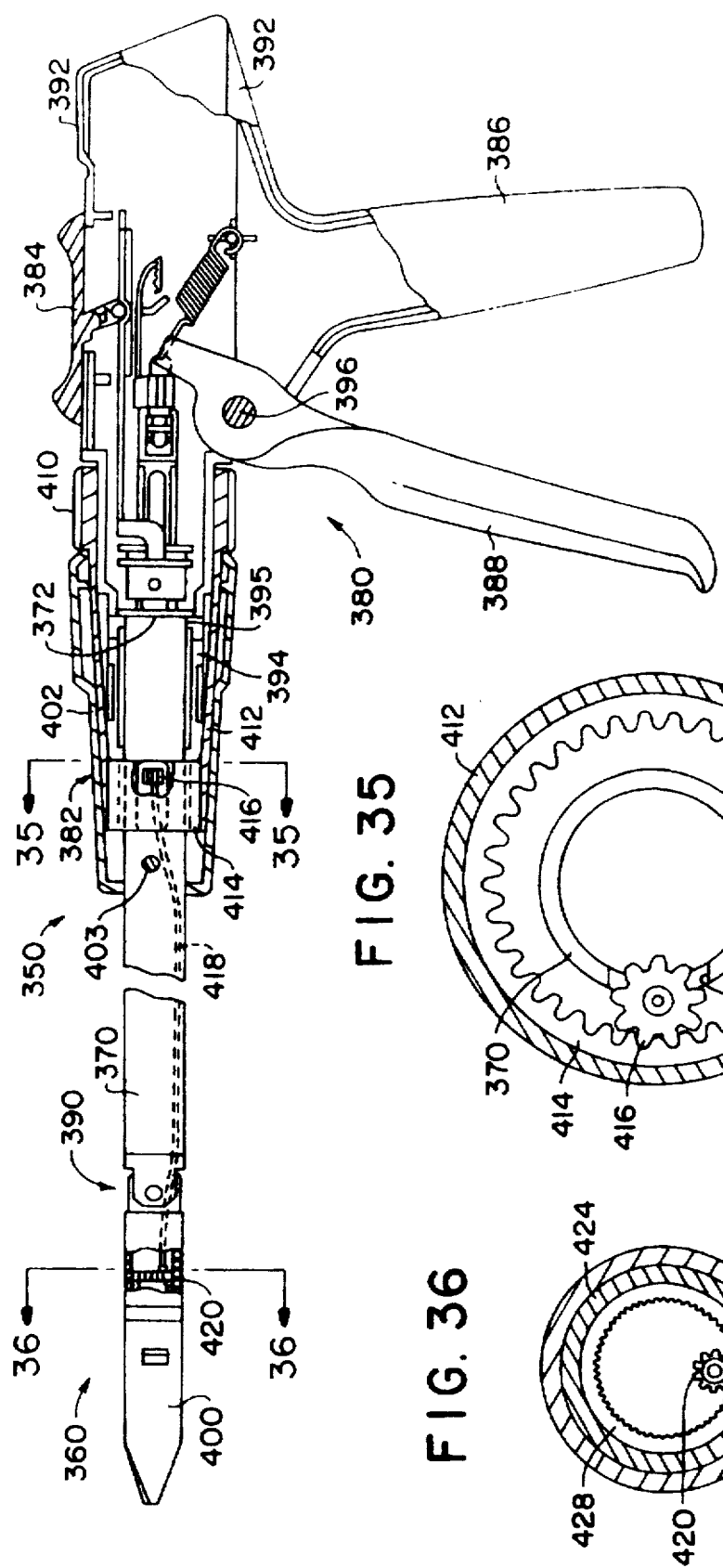

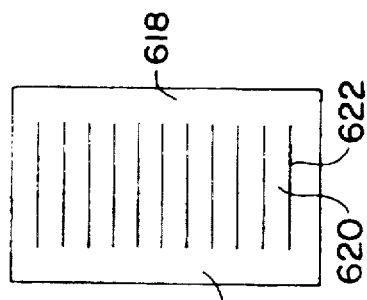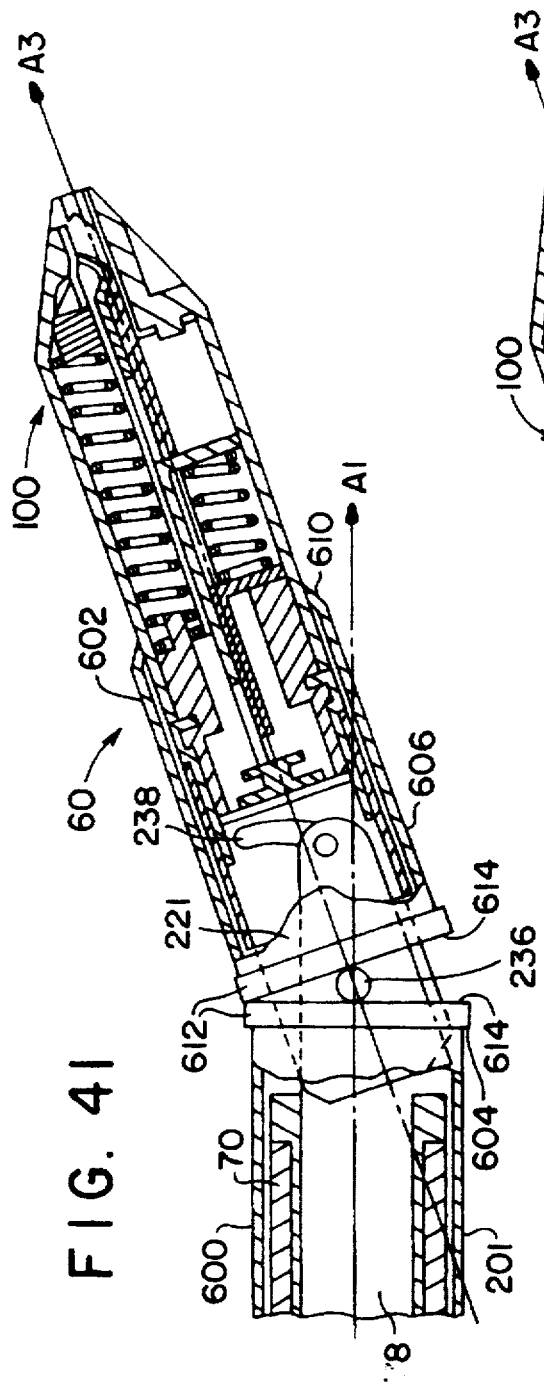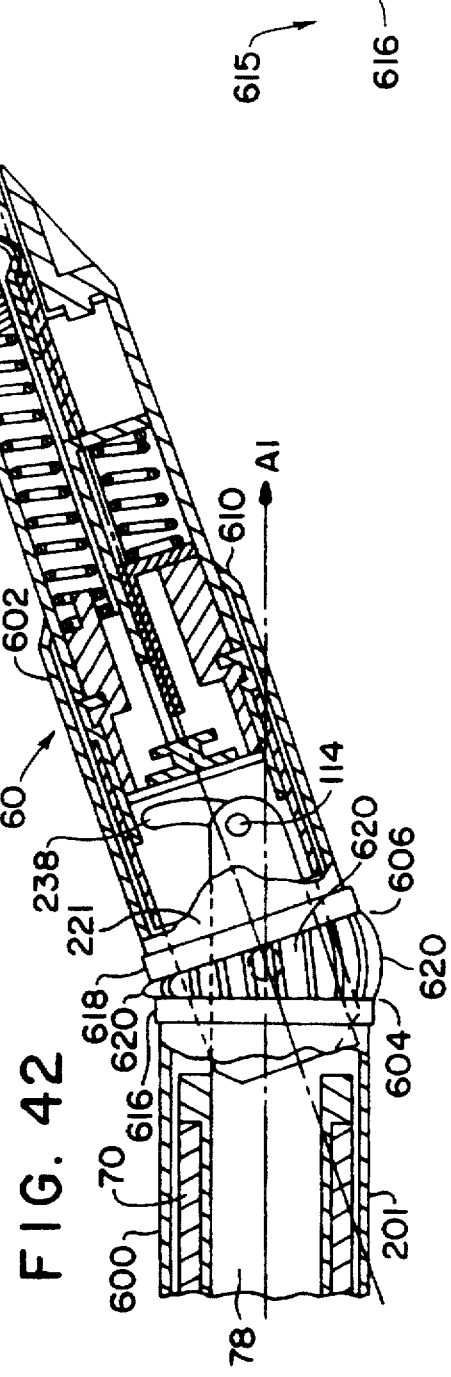

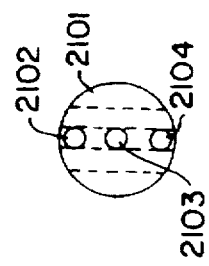
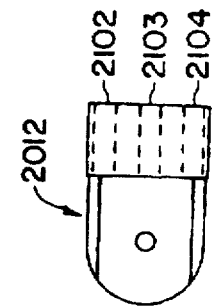
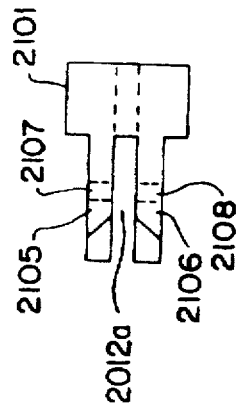
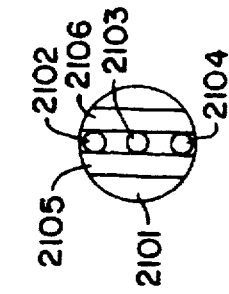
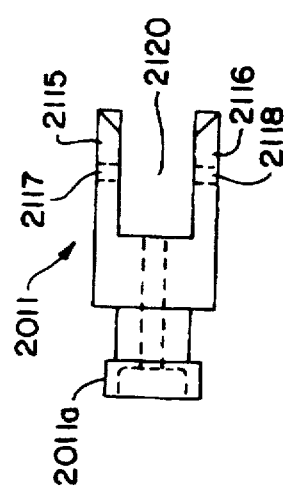
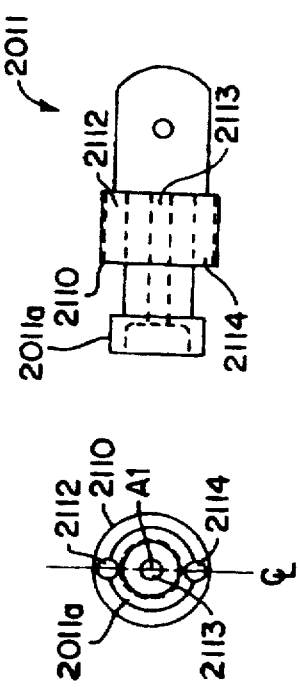

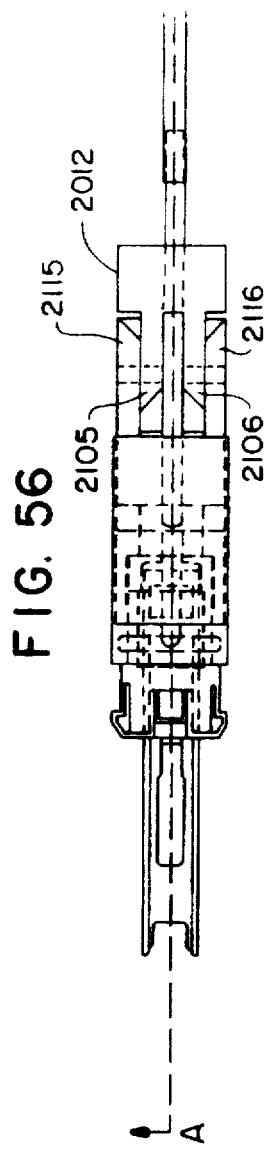
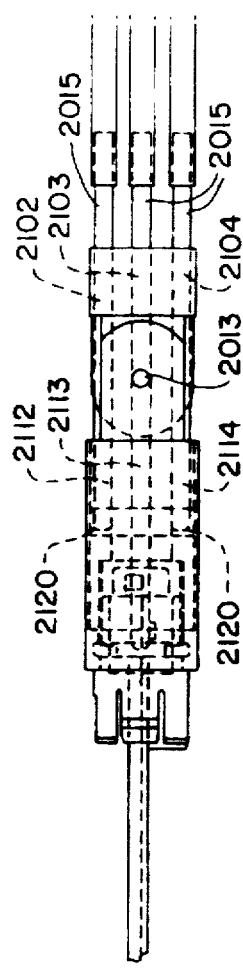
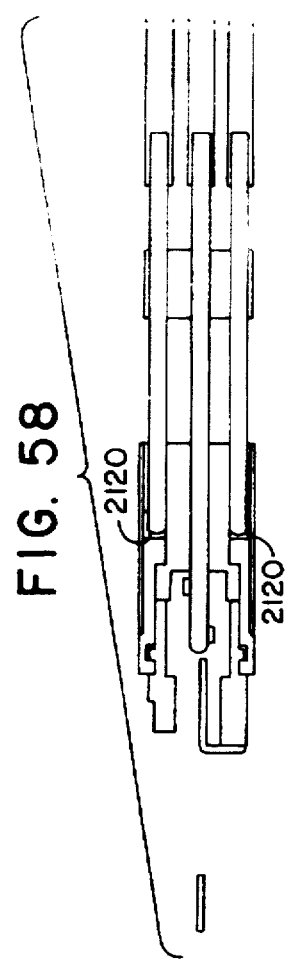
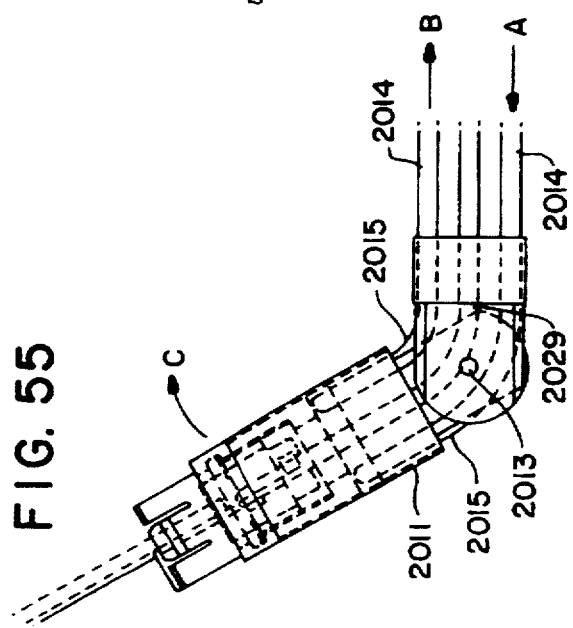
FIG. 56
FIG. 57
FIG. 58
FIG. 55

ENDOSCOPIC SURGICAL INSTRUMENT WITH PIVOTABLE AND ROTATABLE STAPLE CARTRIDGE

This is a division of application Ser. No. 08/080,462, filed Jun. 21, 1993, now U.S. Pat. No. 5,431,323, which is a continuation-in-part of Ser. No. 07/959,184 filed Oct. 9, 1992 now U.S. Pat. No. 5,381,943 issued Jan. 1, 1995, which is hereby incorporated by reference.

FIELD OF THE INVENTION

This invention relates to surgical instruments having an articulating end pivotally connected to a shaft, wherein the articulating end may be rotated about a longitudinal axis over a plurality of angles of articulation with respect to the longitudinal axis of the shaft. More specifically, the present invention relates to endoscopic instruments such as a surgical stapling instrument for applying surgical staples to internal body tissue and, more particularly, to a surgical stapler which can be used endoscopically for the repair of hernias. Most specifically, this invention relates to an endoscopic surgical stapling instrument including a staple cartridge which is pivotally and rotatably mounted to allow the surgical staples to be applied to the internal body tissue in any desired orientation. Additionally, the present invention relates to an improved mechanism for providing articulation to the articulating end of the instrument.

BACKGROUND OF THE INVENTION AND PRIOR ART

With the proliferation of endoscopic surgery, it has been realized that there are many procedures typically performed in open surgery which can be performed endoscopically. In endoscopic surgery, a trocar, which is a pointed piercing device, is inserted into the body with a cannula placed around the trocar. After the trocar pierces the body cavity walls, it is removed and the cannula remains in the body. Through this cannula, endoscopic procedures can be conducted. Generally, the endoscopic procedures are performed under insufflation. Some of the more typical endoscopic procedures have included gall bladder removal, tissue repair, and sterilization procedures such as occluding of fallopian tubes.

Surgeons realize that it may be possible to perform additional procedures endoscopically, once the proper materials and mechanisms become available for performing these procedures. One of the more basic, and quite logical extensions of current endoscopic procedures has been focused on the repair of hernias. It is realized that to have the capability of performing hernia repair endoscopically will benefit the medical community in many ways. Specifically, it is realized that endoscopic hernia repair will allow the patient to recuperate more rapidly, and without the more than likely extensive physical therapy currently practiced as a result of a hernia repair performed by open surgery.

Moreover, it is realized that hernia repair procedures may contain aspects which are applicable in other procedures. For instance, if it is possible to cover, or reinforce and constrain a hernia, it may be possible to apply this procedure to other vessels or organs, in a similar manner. Also, it is realized that once a device becomes available wherein hernias can be repaired, many of the functional components of the hernia repair device will be useful in other devices capable of performing other procedures. Also, naturally, these mechanisms may be useful for procedures in which open surgery is performed.

In response to the above described needs, a number of surgical instruments have been developed for use in endoscopic stapling procedures. One such device, copending U.S. patent application Ser. No. 759,014, filed Sep. 12, 1991, Attorney Docket No. SEN-83, expressly incorporated in its entirety by reference herein, discloses a surgical stapler having a rigid, rotatable shaft containing a stack of staples aligned in a horizontal plane with respect to the shaft. This mechanism has proven quite effective in performing endoscopic surgical procedures; it does not, however, offer means for articulating the tip of the shaft containing the staples in response to a surgeon's need to alter the orientation of the device once it has been inserted into the patient.

Copending U.S. patent application Ser. No. 959,184 (END-26), also expressly incorporated in its entirety by reference herein, discloses an endoscopic surgical device which includes an articulating tip allowing the surgeon to articulate a staple cartridge after the device has been inserted into the patient. The staple cartridge includes a stack of staples oriented in a vertical plane, which allows for a more efficient packing of staples in the device.

Although the articulation device of the aforedescribed application is effective in providing articulation of the tip of the shaft, it is limited to providing a predetermined number of angles of articulation by use of a ratchet mechanism. Occasionally, the ratchet mechanism may bind and become difficult to operate smoothly.

It would, therefore, be useful to provide an endoscopic surgical instrument that is capable of having an articulatable tip that could be rotated about its longitudinal axis in a plurality of angles of articulation with respect to the shaft. Additionally, a significant advance in the art would be realized if a new articulation device could be developed to better solve the aforementioned problems of ratchet-type articulation.

SUMMARY OF THE INVENTION

Accordingly, it is an object of the present invention to provide an endoscopic surgical stapler for applying staples to secure a hernia repair patch to internal body tissue.

Another object of the invention is to provide an endoscopic surgical stapler including a staple cartridge which is pivotally and rotatably mounted to allow the staples to be fastened to the tissue in any desired orientation.

It is also an object of the invention to provide an endoscopic surgical stapling instrument in which the pivotal movement and rotation of the staple cartridge can be controlled from a remote actuator handle assembly.

It is another object of the invention to provide an endoscopic surgical stapling instrument which facilitates manipulation by a surgeon to control the orientation and actuation of the staple cartridge.

A further object of the invention is to provide a staple cartridge for use with a surgical stapling instrument which includes an improved staple forming mechanism for advancing the staples one at a time into engagement with an anvil about which the staple is formed to secure the staple to the tissue.

Yet another object of the invention is to provide an endoscopic surgical instrument having an articulatable tip, which tip may be rotated 360° about its axis after the tip has been articulated with respect to the longitudinal axis of the shaft to which it is pivotally connected.

It is still another object of the invention to provide a retrofittable device for use on existing articulatable endoscopic surgical instruments for providing the aforedescribed 360° rotation of the tip of the device after articulation.

It is still a further object of the invention to provide a mechanism for smoothly articulating the tip of the instrument in a sweeping, as opposed to a ratcheting, motion.

The aforedescribed objects are satisfied with the present invention, which includes a device for providing rotational motion to the distal end of any surgical instrument having a shaft for introducing surgical apparatus to a patent. The shaft of the instrument includes an articulatable tip which, as previously described, may be rotated about its axis after the tip has been articulated with respect to the shaft longitudinal axis. Surgical apparatus which may be used in connection with the shaft include cannulas, cameras, staplers, ligation devices, forceps, drills, suction devices, insulation devices, cutting devices, scalpel devices, clamps, absorption devices, injection devices, drainage devices, lasers, cryogenic devices, sonic devices, illumination devices, and stitching devices. In the aforedescribed surgical instruments, devices similar to those previously described are employed to provide the desired rotational movement of the articulatable tip of the surgical instrument shaft.

In another embodiment of the invention, the invention is adapted to provide rotational motion to a rotatable, articulatable staple cartridge of a surgical stapling instrument having a support shaft supporting the staple cartridge. The stapling instrument includes a pivot for pivoting the staple cartridge relative to the support shaft, and the staple cartridge has a longitudinal axis forming an angle of articulation relative to an axis passing longitudinally through the support shaft. The device of the invention allows the staple cartridge to be rotated about its longitudinal axis over a plurality of angles of articulation of the staple cartridge after the staple cartridge has been articulated with respect to the support shaft.

In one preferred embodiment of the invention, the device includes a first external sleeve rotatably positioned on the support shaft and a second external sleeve positioned on and engaging the staple cartridge. The first external sleeve has a distal end terminating proximate the pivot and the second external sleeve has a proximal end terminating proximate the pivot. The distal and proximal sleeve ends of the first and second sleeves engage one another for transferring rotational motion from the first external sleeve to the second external sleeve and to the staple cartridge.

In another preferred embodiment of the invention, the distal and proximal sleeve ends comprise interconnecting teeth positioned about the external sleeves. In another embodiment of the invention, the distal and proximal sleeve ends comprise frictional annular flanges. In yet another embodiment of the invention, the first and second sleeves are connected with a series of flexible film strips that are adhesively connected to the ends of the first and second sleeves.

In yet another preferred embodiment of the invention, a stapling instrument is provided having an improved articulation device that includes a control knob rotatably mounted to the support shaft proximate the handle of the instrument. The device further includes a mechanism for transferring rotational motion of the control knob to an articulation driver in a longitudinal direction generally parallel to the longitudinal axis of the support shaft. The device further includes a flexible cable slidably positioned within the support shaft and connected at one end to the articulation driver and connected at its other end to the staple cartridge at a point spaced from the longitudinal axis of the staple cartridge.

In yet another preferred embodiment of the invention, the control knob includes a worm gear for transferring rotational motion about the axis of the control knob to the articulation driver.

In another preferred embodiment of the invention, the articulation driver includes a sleeve rotatably positioned on the support shaft, having an annular channel therein for slidably receiving a flange connected to the articulation driver. The channel is inclined with respect to the longitudinal axis of the support shaft, thereby providing longitudinal motion of the flange and articulation driver as the sleeve is rotated by the worm gear.

The present invention further achieves an improved endoscopic surgical stapler which is adapted for insertion through an endoscopic tube or cannula into a body cavity to apply one or more surgical staples to the internal body tissue. The surgical stapling instrument includes a staple cartridge which is pivotally mounted at the distal end of a tubular support shaft extending from a handle which includes a staple actuator mechanism for actuating the staple cartridge to fasten the staples seriatim to the tissue. The staple cartridge is mounted for pivotal movement relative to the support shaft about an axis transverse to the longitudinal axis of the support shaft to permit the angular orientation of the staple cartridge to be adjusted. Also, the staple cartridge is mounted for rotation relative to the support shaft to permit the rotational orientation of the staple cartridge to be adjusted. In addition, the support shaft is rotatable about its longitudinal axis relative to the handle. These features of the stapling instrument allow the staple cartridge to be precisely aligned with the desired region of the internal body tissue to which the staple is applied. Separate actuator mechanisms are provided on the handle for controlling the rotation of the support shaft, the pivoting of the staple cartridge relative to the support shaft, and the rotation of the staple cartridge relative to the support shaft. These actuator mechanisms facilitate manipulation of the stapling instrument by a surgeon to position the staple cartridge in a desired orientation.

In accordance with one aspect of the invention, the surgical stapling instrument is provided with pivot means at the distal end of the support shaft for mounting the staple cartridge for pivotal movement about an axis transverse to the longitudinal axis of the support shaft. Actuator means is provided on the handle for pivoting the staple cartridge about the transverse axis to adjust the angular position of the staple cartridge relative to the support shaft. The stapling instrument includes means for retaining the staple cartridge in different angular positions relative to the support shaft. The staple cartridge has a staple forming mechanism which can be actuated by the staple actuator mechanism with the staple cartridge oriented in any of its different angular positions.

The surgical stapling instrument includes actuator means on the handle for rotating the support shaft about its longitudinal axis to adjust the rotational orientation of the support shaft and the staple cartridge. Also, means is provided for retaining the support shaft in different rotational positions as the support shaft is rotated about its longitudinal axis.

In a preferred embodiment of the surgical stapling instrument, the staple cartridge is mounted for rotation about its longitudinal axis relative to the support shaft. Actuator means is provided on the handle for rotating the staple cartridge to adjust the rotational position of the staple cartridge relative to the support shaft. Also, means is provided for retaining the staple cartridge in different rotational positions as the staple cartridge is rotated about its longitudinal axis relative to the support shaft.

In accordance with another aspect of the invention, a staple cartridge for use with a stapling instrument for applying one or more surgical staples to tissue comprises a cartridge housing adapted to receive a plurality of staples in a row for longitudinal movement therethrough, an anvil mounted on the housing, means for advancing the forwardmost staple in the row into engagement with the anvil, means for rotating the forwardmost staple from a transverse orientation into a longitudinal orientation as the staple is advanced toward the anvil, and means for forming the forwardmost staple about the anvil to attach the staple to the tissue. The staple advancing means comprises a staple holder slidably mounted within the cartridge housing for advancing the forwardmost staple from the row and clamping the staple against the anvil. The staple rotating means comprises ramp means on the cartridge housing for engaging and rotating the forwardmost staple into a longitudinal orientation as the staple is advanced by the staple holder. The staple forming means comprises a staple former slidably mounted within the cartridge housing for movement relative to the staple holder and adapted to form the forwardmost staple about the anvil. Preferably, the staple holder includes an ejector arm for removing the forwardmost staple from the anvil after the staple is formed.

A preferred embodiment of the staple cartridge is adapted for use with a staple having a generally U-shaped body including a crown with a central offset portion and a pair of depending legs at opposite sides of the crown. The staple cartridge comprises an elongated hollow cylindrical cartridge housing including a pair of spaced parallel guide rails therein for slidably supporting a stack of staples for longitudinal movement there along with the staple crowns resting on the guide rails and the staple legs oriented perpendicularly to the longitudinal axis of the cartridge housing. A staple follower is slidably mounted on the guide rails for urging the staples forwardly on the guide rails toward the distal end of the cartridge housing. An anvil is mounted adjacent to the distal end of the cartridge housing. A staple holder is slidably mounted between the guide rails for engaging the central offset portion of the forwardmost staple to advance the staple from the stack into engagement with the anvil. Ramp means is provided on the cartridge housing for engaging the crown of the forwardmost staple advanced by the staple holder and rotating the staple into a longitudinal orientation with the staple legs oriented parallel to the longitudinal axis of the cartridge housing. A staple former is slidably mounted between the guide rails and movable relative to the staple holder for engaging the crown of the forwardmost staple to form the staple about the anvil to attach the staple to the tissue.

In the preferred embodiment of the staple cartridge, the staple former comprises an elongated channel-shaped member including upstanding side flanges extending along its opposite sides for engaging and forming the staple. The staple holder comprises an elongated plate-like member slidably supported on the staple former and located between the side flanges. The staple holder includes a notch at its distal end for receiving the forwardmost staple to be advanced. The staple holder also includes a pusher finger at its distal end for engaging the forwardmost staple and clamping the staple against the anvil. In addition, the staple holder includes an ejector arm at its distal end for removing the formed staple from the anvil when the staple holder is retracted.

BRIEF DESCRIPTION OF THE DRAWINGS

The foregoing and other objects, aspects and advantages will be better understood and more readily apparent to those of ordinary skill in the art, as the following detailed description of the preferred embodiments of the invention proceeds, particularly with reference to the accompanying illustrative figures, in which:

FIG. 1 is an overall perspective view of an endoscopic surgical stapling instrument constructed in accordance with a preferred embodiment of this invention;

FIG. 2 is a partially cutaway side view of the stapling instrument of FIG. 1;

FIG. 3 is an enlarged longitudinal section of the stapling head and cartridge assembly of FIG. 2;

FIG. 4 is an enlarged longitudinal section of the stapling head and cartridge assembly from the opposite side of FIG. 3;

FIG. 4a is a schematic plan view of a portion of the first and second sleeves of a preferred embodiment of the invention, illustrating the interlocking teeth.

FIGS. 5 and 6 are exploded perspective views showing the components of the stapling instrument of FIG. 1;

FIG. 7 is an enlarged partially cutaway horizontal section of a portion of the stapling head assembly and support shaft of FIG. 2;

FIG. 8 is an enlarged partially cutaway vertical section of a portion of the stapling head assembly and support shaft of FIG. 2;

FIG. 9 is an enlarged, exploded perspective view showing the staple cartridge and the staple forming mechanism of the stapling head assembly;

FIG. 10 is an enlarged longitudinal section of the staple cartridge of FIG. 9;

FIG. 11 is an enlarged longitudinal section of the staple cartridge along line 11—11 of FIG. 10;

FIG. 12 is an enlarged proximal end view of the staple cartridge;

FIG. 13 is an enlarged distal end view of a portion of the stapling head assembly of FIG. 3;

FIG. 14 is an enlarged fragmentary section of the staple cartridge taken along line 14—14 of FIG. 11;

FIG. 15 is a longitudinal section of a slide actuator for pivoting the stapling head assembly;

FIG. 16 is a proximal end view of the slide actuator of FIG. 15

FIG. 17 is an enlarged plan view of a staple for use with the surgical stapling instrument of this invention;

FIG. 18 illustrates a hernia repair patch fastened to tissue with staples applied by the surgical stapling instrument of this invention;

FIG. 32 is an overall perspective view of an alternative embodiment of the surgical stapling instrument constructed in accordance with this invention;

FIG. 33 is a partially cutaway side view of the stapling instrument of FIG. 32;

FIG. 34 is an enlarged longitudinal section of the stapling head assembly from the opposite side of FIG. 32;

FIG. 35 is an enlarged cross section of the stapling instrument along line 35—35 of FIG. 33;

FIG. 36 is an enlarged cross section of the stapling instrument along line 36—36 of FIG. 33;

FIG. 41 is an enlarged longitudinal section of the stapling head and cartridge assembly of the invention with frictional annular flanges for transferring rotational motion to the staple cartridge.

FIG. 42 is an enlarged longitudinal section of the stapling head and cartridge assembly of the invention with adhesive bands and film strips for transferring rotational motion to the staple cartridge.

FIG. 43 is a plan view of the adhesive bands and film strips of FIG. 42 as formed from a unitary piece of material.

FIG. 52 is a cross-sectional view of the embodiment of the invention illustrated in FIGS. 51 and 51a.

FIG. 53 is a front, top, left and right side plan view of a stationary clevis useful in the embodiment of FIGS. 51, 51a and 52.

FIG. 54 is a front, top, and left side view of a movable clevis useful in the embodiment of FIGS. 51, 51a, and 52.

FIG. 55 is a side elevational view detailing the embodiment of FIGS. 51, 51a, and 52 in an articulation mode.

FIG. 56 is a plan view of the preferred articulating mechanism used in the embodiment of FIGS. 51, 51a, and 52.

FIG. 57 is a front plan view of the device of FIG. 56.

FIG. 58 is a cross-sectional view of the device of FIG. 56 taken along the lines A—A.

DETAILED DESCRIPTION OF PREFERRED EMBODIMENTS

Figure 5:
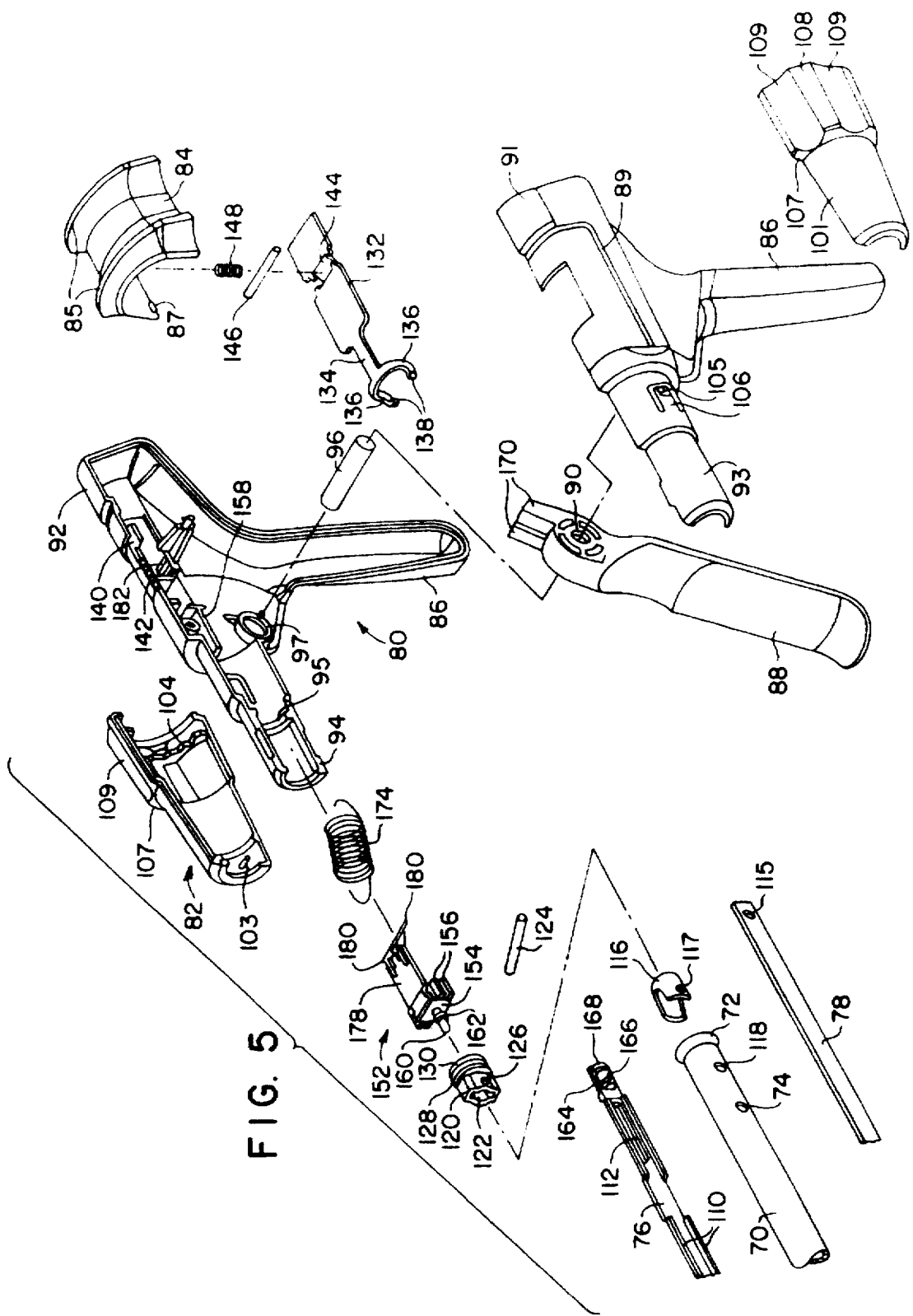

Referring to FIG. 1, the present invention is embodied in, and/or retrofittable to, an articulating endoscopic surgical stapling instrument, generally 50, including a distal stapling head assembly 60 which is pivotally connected to an elongated support shaft, or tube 70 rotatably or non-rotatably mounted on a proximal actuator handle assembly generally 80. When a rotatable tube 70 is used, a rotatable adjusting knob 82 may be mounted at the distal end of the actuator handle assembly 80 for rotating the support tube 70 about its longitudinal axis A1.

A saddle-shaped actuator 84 is slidably mounted on the actuator handle assembly 80 for controlling the pivotal, or articulatable movement of the stapling head assembly 60 relative to the support tube 70 about an axis of articulation A2 running perpendicular to the support tube longitudinal axis A1. The actuator handle assembly 80 includes a depending handle grip 86 and a pivotally mounted staple actuating lever 88 for actuating a staple cartridge 100 on the stapling head assembly 60. Preferably, the actuator handle assembly 80, the adjusting knob 82, the saddle-shaped actuator 84 and the staple actuating lever 88 consist of plastic material.

As illustrated in FIG. 1, the support tube 70 preferably includes a sleeve 600 which slidably and rotatably engages the shaft 70 such that the sleeve 600 may be slid toward or away from the stapling head assembly 60 and may be rotated about the shaft longitudinal axis A1 with respect to the stationery shaft 70.

As further illustrated in FIG. 1, the stapling head assembly 60 may be articulated about a pivot or articulation axis A2, forming an angle of articulation with respect to the support tube axis A1. The stapling head assembly 60 has a longitudinal axis A3 that forms the angle of articulation with respect to the longitudinal axis A1 of the support tube 70, as illustrated.

The stapling head assembly 60 may be rotated about its axis A3 as will subsequently be described. In the past, this rotation was not possible once the stapling head assembly 60 was placed inside the body. The present invention, however, allows rotation of the staple cartridge 100 about the axis A3 at any angle of articulation inside the body. This rotational motion is possible by virtue of the first sleeve 600, which engages a second sleeve 602 fastened to the cartridge 100. As best seen in FIG. 4, the first sleeve 600 has a distal end 604 terminating proximate a pivot 236. The pivot 236 allows the staple cartridge 100 and stapling head assembly 60 to be articulated about the axis of articulation A2 relative to the support tube 70.

The second external sleeve 602 has a proximal end 606 also terminating proximate the pivot 236. The distal and proximal ends 604 and 606 of the first and second sleeves 600 and 602, respectively, allow for the transfer of rotational motion from the first external sleeve 600 to the second external sleeve 602 to the stapling cartridge 100.

In the embodiment of the invention illustrated in FIGS. 1 and 4, the distal and proximal sleeve ends comprise a series of interconnecting teeth 608, preferably equally sized and shaped, separated by a plurality of notches, 609, also preferably equally sized and shaped, to complement the teeth 608. The teeth 608 of the distal end 604 are received by the notches 609, of the proximal end 606 and vise versa. When the distal end 604 of the first sleeve 600 is aligned with the proximal end 606 of the second sleeve 602, such that equals 0°, the teeth 608 and notches 609 of each sleeve preferably mate with one another, with little or no gaps between them, as illustrated schematically in FIG. 4a.

As will now be appreciated to those of ordinary skill in the art, rotation of the staple cartridge 100 can be varied, in terms of ease of rotation, by varying the number and depth of teeth 608 and complementary notches 609 on the first and second sleeves. In one preferred embodiment of the invention, the sleeves 600 and 602 each have 18 teeth 608 and notches 609.

As further illustrated in FIG. 4, the second sleeve 602 is rotatably positioned around the non-rotating portion, e.g., the clamshell sleeve 224, and clamshell halves, 221, 222 (FIG. 6) of the stapling head assembly 60, and is fastened at its end 610 to the staple cartridge 100, which rotates, as will be subsequently described. The end 610 of the sleeve 602 may be fastened to the cartridge 100 in any number of ways, including the use of adhesives, pins, rivets, welding, etc. Although the distal end 604 of the first sleeve 600 may be withdrawn with respect to the second sleeve 602, is preferred that the second sleeve 602 be in a fixed position with respect to the cartridge 100 by being fastened thereto as previously described.

In the embodiment of the invention illustrated in FIG. 1, the first sleeve 600 preferably includes a stop 601 at the end of the sleeve 600 proximate the handle assembly, generally 80, fastened to the support shaft 70. The stop 601 assists the surgeon in determining that the sleeve 600 has reached the handle 80 and has been stopped thereby, and may comprise an annular flange around the sleeve 600.

In another highly preferred embodiment of the invention, the first sleeve 600 is biased either toward or away from the handle assembly 80, such as with a spring or other biasing means (not shown).

In another preferred embodiment of the invention, illustrated in FIG. 41, the first sleeve distal end 604 and the second sleeve proximal end 606 comprise annular flanges 612 that engage each other with frictional surfaces 614. In the embodiment of FIG. 41, the frictional surfaces 614 may comprise an elastometeric material, such as natural or synthetic rubber, a stippled plastic or metallic surface, or a granulated surface, such as emery cloth or sandpaper, in addition to other frictional surfaces known to those skilled in the art of frictional surfaces. The annular flanges 612 may be arranged such that the outside diameter of the flange 612 on the first sleeve distal end 604 is smaller than the inside diameter of the flange 612 on the second sleeve proximal end 606.

In still another embodiment of the invention, the teeth 608 or annular flanges 612 are replaced with bands of film, which may be adhesive film, connected by a series of strips. As illustrated in FIG. 42, a first band of adhesive film 616 is fastened about the first sleeve 600 proximate the pivot 236, and a second band of adhesive film 618 is fastened about the second sleeve 602, also proximate the pivot 236. The bands 616 and 618 are joined by a plurality of film strips 620 positioned about the pivot 236 and transferring rotational forces from the first sleeve 600 to the second sleeve 602 to the staple cartridge 100. As illustrated, the film strips 620 are aligned substantially parallel to the longitudinal axis A1 of the support shaft 70.

As best seen in FIG. 43, the bands 616, 618 and the films strips 620 preferably comprise a unitary piece of generally rectangular adhesive film, generally 615, having slits 622 forming the strips 620, as illustrated. In the embodiment of FIG. 43, the unitary piece of film may be fabricated of any material suitable for the purpose, including, by way of example, but not limitation, nylon, polyethylene, Teflon®, Ultem®, and polypropylene. Additionally, the film strips 620 may be coated on their internal surfaces with a friction reducing material, known to those skilled in the art, for reducing friction of the strips 620 with respect to the pivot 236. Such materials include, by way of example, but not limitation, Teflon®, silicone, and polyethylene.

Referring to FIG. 17, a staple 65 adapted for use with the surgical stapling instrument 50 of the present invention comprises a wire-like body of circular cross section which is bent in a generally U-shaped configuration. Preferably, the staple 65 consists of titanium or stainless steel. The staple 65 includes a top portion or crown 66 provided with a central dimpled portion 67 which is offset downwardly from the crown 66 by an amount approximately equal to the diameter of the circular cross section of the staple 65. The opposite sides of the staple 65 are bent downwardly to provide a pair of depending legs 68 which are substantially perpendicular to the crown 66. Each leg 68 has a beveled end 69 which is beveled at an angle of approximately 45 degrees. When the staple 65 is closed by operation of the surgical stapling instrument 50, the staple legs 68 overlap each other as shown by phantom lines in FIG. 14 to secure the staple to the tissue.

As shown in FIGS. 1 and 5, the handle assembly 80 includes a pair of hollow handle sections 91 and 92 which are adapted to snap fit together. The handle sections 91 and 92 include distally extending elongated, semi-cylindrical neck portions 93 and 94 which receive the proximal end of the support tube 70 therebetween and mount the support tube 70 for rotation about its longitudinal axis relative to the handle assembly 80. Alternatively, the support tube 70 may be fixed, rather than rotatable, with respect to the handle assembly 80, in which case the surgeon rotates the entire handle assemble 80 to rotate the support tube 70 inside the cannula and/or the body cavity.

Each of the handle sections 91 and 92 includes an internal annular flange 95 (one shown) for engaging a radially projecting flange 72 at the proximal end of the support tube 70 to retain the support tube 70 within the handle assembly 80. The staple actuating lever 88 is pivotally mounted on the actuator handle assembly 80 by a pivot pin 96 extending through a pivot hole 90 in the lever 88. The pivot pin 96 is received in a pair of hollow cylindrical support stems 97 (one shown) formed on the inside of the handle sections 91 and 92.

As shown in FIGS. 1 and 5, the adjusting knob 82 comprises a pair of elongated hollow, tapered sleeve-like sections 101 and 102 which fit together over the neck portions 93 and 94 of the handle sections 91 and 92, respectively. Each of the sleeve-like knob sections 101 and 102 has an inwardly projecting prong 103 adjacent to its distal end. The prongs 103 are received in a pair of holes 74 (one shown) formed on opposite sides of the support tube 70 to secure the knob sections 101 and 102 to the support tube 70. Each of the knob sections 101 and 102 includes a semi-circular ratchet 104 on its inner wall for engaging a pair of detentes 105 mounted on resilient arms 106 formed on each of the handle sections 91 and 92. The semi-circular ratchets 104 and the detentes 105 provide a ratchet mechanism for retaining the support tube 70 in different rotational positions as the support tube 70 is rotated about its longitudinal axis. For example, each ratchet 104 is provided with eight ratchet teeth which allow the support tube to be rotated in sixteen equal angular increments of 22½ degrees. Each of the knob sections 101 and 102 has an enlarged rear section 107 provided with alternating longitudinal ridges 108 and finger-receiving grooves 109 which facilitate the rotation of the adjusting knob 82 and the support tube 70 by the surgeon.

The support tube 70 is an elongated, thin-walled rigid metal tube, e.g., stainless steel. Inside the support tube 70 are mounted an elongated staple driver 76 and an elongated articulation driver 78 which are slidable longitudinally relative to the support tube 70 and relative to each other. The articulation driver 78 pivots the stapling head assembly 60 in response to movement of the saddle-shaped actuator 84 along the actuator handle assembly 80. The staple driver 76 actuates the staple forming mechanism within the staple cartridge 100 when the staple actuating lever 88 is operated. Preferably, the staple driver 76 and the articulation driver 78 consist of stainless steel.

As shown in FIGS. 5 and 6, the staple driver 76 comprises an elongated thin flat rod including a pair of spaced parallel flanges 110 which extend longitudinally along its top and bottom edges. The staple driver 76 has a pivot hole 111 (FIG. 6) adjacent to its distal end and a longitudinal slot 112 (FIG. 5) adjacent to its proximal end. The articulation driver 78 comprises an elongated thin flat rod which is slidably mounted adjacent to the staple driver 76 and is slidably received between the flanges 110. The articulation driver 78 has an enlarged distal portion 113 (FIG. 6) with a laterally projecting guide pin 114 formed adjacent to its distal end. An assembly hole 115 (FIG. 5) is formed adjacent to the proximal end of the articulation driver 78. A driver guide member 116 of generally cylindrical shape is mounted within the proximal end of the support tube 70. The driver guide member 116 has a pair of opposed, outwardly extending posts 117 which are received in a pair of corresponding holes 118 formed adjacent to the proximal end of the support tube 70. The driver guide 116 has a rectangular slot 119 extending therethrough for slidably receiving the staple driver 76 and the articulation driver 78.

As shown in FIGS. 2 and 5, a driver coupling member 120, preferably made of plastic material, includes an opening 122 extending longitudinally therethrough for receiving the proximal ends of the staple driver 76 and the articulation driver 78. The driver coupling member 120 is secured to the articulation driver 78 by a coupling pin 124 which is received in the hole 115 in the articulation driver 78 and extends through a pair of apertures 126 formed on opposite sides of the coupling member 120. The coupling pin 124 is slidably received in the longitudinal slot 112 of the staple driver 76 to allow the articulation driver 78 to slide longitudinally relative to the staple driver 76. A pair of spaced annular flanges 128 and 130 are provided at the proximal end of the coupling member 120 for connection to an articulation control mechanism on the actuator handle assembly 80.

The saddle-shaped actuator 84 operates a slide member 132 which is coupled to the driver coupling member 120 to operate the articulation driver 78. The saddle slide member 132 is a generally flat metal plate with an elongated neck 134 projecting distally and having a pair of curved depending arms 136 provided with inwardly projecting fingers 138 which are received between the annular flanges 128 and 130 on the driver coupling member 120. The annular flanges 128 and 130 capture the fingers 138 therebetween and connect the coupling member 120 to the saddle slide member 132 for longitudinal movement therewith. The annular flanges 138 allow the coupling member 120 to rotate about its longitudinal axis relative to the saddle slide member 132 when the support shaft 70 is rotated by the adjusting knob 82.

The saddle slide member 132 is slidably mounted on a pair of horizontal support ledges 140 (one shown) formed on the interior of the handle sections 91 and 92. Each support ledge 140 includes a series of uniformly spaced notches 142 arranged in a longitudinal row. The saddle slide member 132 is formed with a transverse notch 144 for receiving a ratchet pin 146 which is biased downwardly into the notch 144 by a coil spring 148 mounted on an inclined post 149 formed on the inside of the saddle-shaped actuator 84. A pair of inclined fingers 150 (FIGS. 15 and 16) is formed on the inside of the saddle-shaped actuator 84 and spaced from opposite sides of the post 149. The ratchet pin 146 extends transversely between the fingers 150 and is slidably received in an inclined slot 151 formed in each of the fingers 150.

The opposite ends of the ratchet pin 146 are received in the notches 142 formed in the support ledges 140. The notches 142 and ratchet pin 146 provide a ratchet mechanism for controlling the angular orientation of the stapling head assembly 60 relative to the longitudinal axis of the support tube 70. The notches 142 provide a series of stop positions which correspond to angular orientations preferably of 0, 15, 30, 45 and 60 degrees relative to the longitudinal axis of the support tube 70.

The saddle-shaped actuator 84 includes a pair of outwardly projecting ribs 85 which serve as finger grips to facilitate the longitudinal movement of the saddle-shaped actuator 84 along the handle assembly 80. The saddle-shaped actuator 84 includes a pair of inwardly projecting guides 87 (FIGS. 15 and 16) formed on each of its opposite sides which are snap-fit and slidably received into a pair of longitudinally extending channels 89 (one shown) formed on the exterior of the handle sections 91 and 92.

Referring to FIGS. 2 and 5, the staple actuating mechanism includes a driver link assembly 152 which is coupled to the staple driver 76 and actuated by the staple actuating lever 88. The driver link assembly 152 comprises a block-shaped slide member 154, preferably of plastic material, including a pair of vertically spaced flanges 156 extending from its opposite sides. Each of the handle sections 91 and 92 includes a horizontal support ledge 158 which is received between one pair of the side flanges 156 to slidably support the driver link assembly 152 on the actuator handle assembly 80. A cylindrical connector pin 160 projecting distally from the front of the slide block 154 includes an annular rim 162 for connecting the drive link assembly 152 to the staple driver 76. The connector pin 160 is inserted into a buckle-like connector 164 at the proximal end of the staple driver 76. The buckle-like connector 164 has a pair of longitudinally spaced bands 166 and 168 which are curved outwardly in opposite directions and capture the annular flange 162 therebetween to couple the staple driver 76 and the driver link assembly 152 together for movement along the longitudinal axis of the support tube 70. Also, the buckle-like connector 164 is free to rotate about the axis of the connector pin 160 to allow the staple driver 76 and the articulation driver 78 to rotate when the support tube 70 is rotated about its longitudinal axis.

As shown in FIGS. 2 and 5, the staple actuating lever 88 includes a pair of upright fingers 170 which are spaced apart to receive a rearwardly projecting lug 172 formed on the slide member 154. The lug 172 is connected to a return coil spring 174 which is anchored to a post 176 on the handle section 92. The return spring 174 normally urges the slide 14 rearwardly into engagement with the upright arms 170 to retain the staple actuating lever 88 in the unactuated position (FIG. 2).

The driver link assembly 152 includes a rearwardly projecting metal leaf spring 178 which is curved downwardly at its proximal end and provided with a pair of spring arms 180 projecting laterally from its opposite sides for engaging a pair of ratchets 182 (one shown) formed on the handle sections 91 and 92. The spring arms 180 and the ratchets 182 provide a ratchet mechanism which retains the driver link assembly 152 at different stages of advancement as the staple actuating lever 88 is actuated. Once the spring arms 180 are engaged with the ratchets 182, the driver link assembly 152 cannot return to its unactuated position until the stapling head assembly 60 is completely fired by operating the staple actuating lever 88.

Referring to FIGS. 1 and 6, the stapling head assembly 60 is pivotally mounted at the distal end of the support tube 70 for pivotal movement about an axis transverse to the longitudinal axis of the support tube 70. The stapling head assembly 60 is pivotally mounted on the support tube 70 by a pivot connection, generally 200, including a pair of pivot housings 201 and 202 of generally semi-cylindrical shape which are fit together and are inserted into the distal end of the support tube 70. The pivot housings 201 and 202 are generally shaped as hollow semi-cylindrical sleeves for slidably receiving the staple driver 76 and the articulation driver 78. Adjacent to the proximal end of each of the pivot housings 201 and 202 is a semi-circular groove 204 which receives an O-ring 206 for engaging the interior of the support tube 70. The O-ring 206 helps to vent the staple cartridge 100 at the insufflation pressures of the abdominal cavity.

As shown in FIG. 5, each of the pivot housings 201 and 202 includes a side opening 208 formed therein adjacent to the groove 204. When the pivot housings 201 and 202 are assembled, silicone is injected into the side openings 208 about the staple driver 76 and the articulation driver 78. With the pivot housings 201 and 202 inserted into the distal end of the support tube 70, a pair of dimples 210 (FIG. 7) is formed on opposite sides of the support tube 70 to deform the tube material into the side openings 208 to fasten the pivot housings 201 and 202. Alternatively, in place of the injected silicone material, a hollow cylindrical silicone plug 209 (FIG. 5) can be inserted into the proximal ends of the pivot housings 201 and 202. The silicone plug 209 includes a pair of distally projecting flanges 211 which slidably engage the outer surfaces of the staple driver 76 and the articulation driver 78. Each of the pivot housings 201 and 202 includes a distally projecting tang 212 which is provided with a pivot hole 214. The pivot housings 201 and 202 include front semi-circular flanges 216 which engage the distal end of the support tube 70.

The pivot connection 200 includes a pair of clamshell members 221 and 222 which are generally semi-cylindrical in shape and fit together inside a tubular clamshell sleeve 224. The clamshell members 221 and 222 each include a front semi-circular flange 226 which engages the distal edge of the clamshell sleeve 224. The front flanges 226 each include an interior semi-circular groove 228. Each of the pivot housings 221 and 222 includes a detent arm 230 projecting inwardly through a side opening 232. Also, each pivot housing 221 and 222 includes a rearwardly extending tang 234 provided with an outwardly projecting pivot pin 236. The pivot pins 236 on the clamshell members 221 and 222 are pivotally received in the pivot holes 214 on the pivot housings 201 and 202. As shown in FIG. 4, the pivot housing 221 has an arc-shaped groove 238 formed on its interior surface for receiving the guide pin 114 on the articulation driver 78. The arc-shaped groove 238 and the guide pin 114 convert longitudinal movement of the articulation driver 78 into pivotal movement of the stapling head assembly 60. Preferably, the pivot housings 201 and 202 and the clamshell members 221 and 222 consist of plastic material.

Referring to FIG. 6, the staple cartridge 100 of the stapling head assembly 60 has a hollow cylindrical housing 240 which is tapered at its distal end. Preferably, the staple cartridge housing 240 is a one-piece molded plastic member. A hollow, generally cylindrical cartridge retainer 242 is inserted into the open proximal end of the staple cartridge housing 240. The cartridge retainer 242 has a pair of spring-like latch arms 244 located at diametrically opposed positions at the front of the retainer 242. The latch arms 244 are snap-fitted into a pair of diametrically opposed openings 245 adjacent to the proximal end of the cartridge housing 240 to hold the cartridge housing 240 and the retainer 242 together. The retainer 242 includes an annular flange 246 which is received in the annular grooves 228 of the clamshell members 221 and 222 to allow the staple cartridge 100 to rotate about its longitudinal axis relative to the support tube 70 and to the pivot connection 200. A set of twelve uniformly spaced circumferential teeth 248 is formed at the proximal end of the retainer 242. The teeth 248 are engaged by the detent arms 230 on the clamshell members 221 and 222. The detent arms 230 and teeth 248 provide a ratchet mechanism which allows the rotational orientation of the staple cartridge 100 to be adjusted in increments of 30 degrees.

Inside the staple cartridge 100 is mounted a staple forming mechanism comprising an anvil 250, a staple holder 252 and a staple former 254 which are preferably made of stainless steel. The staple former 254 is channel-shaped in configuration for slidably receiving the staple holder 252 therein. The staple former 254 has an elongated central slot 256 with a depending prong 258 at the proximal end of the slot 256. The staple holder 252 includes a depending prong 260 which is slidably received in the slot 256 and is biased away from the prong 258 by a compression coil spring 262. A feeder shoe 264 is slidably mounted within the staple cartridge 100 for urging a series of staples 65 toward the distal end of the cartridge 100. The feeder shoe 264 is biased in the distal direction by a compression coil spring 266 which is mounted on a distally projecting prong 268 on the cartridge retainer 242.

The staple driver 76 is connected to the staple former 254 by a plunger 270 which is slidably mounted between the clamshell members 221 and 222. The plunger 270 is a generally flat metal plate, e.g. aluminum, and includes a longitudinally extending side flange 272 slidably received in a longitudinal groove 274 formed in the clamshell member 222. The plunger 270 has a pivot hole 276 adjacent to its proximal end. A pivot link 278 includes a pair of laterally projecting pivot pins 280 and 282 which are pivotally received in the pivot holes 111 and 276, respectively, to attach the staple driver 76 to the plunger 270. The pivot link 278 transfers the longitudinal movement of the staple driver 76 into longitudinal movement of the plunger 270. Also, the pivot link 278 permits the plunger 270 to pivot relative to the staple driver 76. At the distal end of the plunger 270, a smaller diameter front disk 284 is spaced from a larger diameter rear disk 286. The front disk 284 is inserted between a pair of inwardly projecting fingers 288 at the proximal end of the staple former 254 to transfer the longitudinal movement of the plunger 270 into longitudinal movement of the staple former 254. The front disk 284 and the inwardly projecting fingers 288 permit the staple former 254 to rotate relative to the plunger 270.

Referring to FIG. 9, the staple cartridge housing 240 has an elongated hollow cylindrical wall 290 which preferably consists of transparent plastic material. Extending longitudinally inside the staple cartridge housing 240 is a first pair of elongated upstanding flanges 292 which are spaced apart and extend parallel to the longitudinal axis of the cylindrical wall 290. The elongated flanges 292 provide a set of guide rails for slidably supporting the staples 65 for longitudinal movement relative to the staple cartridge housing 240. Each flange or guide rail 292 has a ledge 293 (FIG. 10) which is inclined at an angle to the axis of the cartridge housing 240 and terminates in an extension 294 of the guide rail 292 at the open distal end of the cartridge housing 240. Each of the flanges 292 is spaced inwardly from the cylindrical wall 290 to provide a pair of elongated side channels 295 (FIG. 12) for receiving the depending legs 68 of the staples 65. The cartridge housing 240 includes a second pair of depending flanges 296 which are spaced apart and extend parallel to the longitudinal axis of the outer cylindrical wall 290. The upper flanges 296 terminate above the lower flanges 292 to provide a sufficient clearance therebetween to receive the crowns 66 of the staples 65. On the inside of each lower flange 292 is an elongated ledge 298 which slidably supports the staple former 254.

The staple cartridge housing 240 has a tapered nose 300 at its distal end including an internal horizontal ledge 302 provided with a longitudinal channel 304 for receiving the anvil 250 of the stapling head assembly 100. The ledge 302 has a rearwardly projecting post 306 to which the anvil 250 is secured. The tapered nose 300 has a central depending tab 308 located above the ledge 302 and provided with a downwardly sloped rear edge 309 which serves as a guide for the dimpled portion 67 of the staple 65 advanced by the staple forming mechanism. Also, the tapered nose 300 includes a pair of sloped ramps 310 (FIG. 11) on opposite sides of the central tab 308 for engaging the crown 66 of the staple 65 which is advanced by the staple forming mechanism to pivot the staple 65 into an orientation parallel to the longitudinal axis of the cartridge housing 240. Each of the ramps 310 terminates at a ledge 312 located adjacent to one of the extensions 294 of the guide rails 292. A window 314 is formed on each side of the cartridge housing 240 adjacent to one of the ramps 310 as a result of the molding process used to form the cartridge housing 240.

As shown in FIG. 9, the staple former 254 is an elongated, channel-shaped member provided with upstanding side flange 320 extending along its opposite sides. The staple holder 252 is an elongated plate-like member which is slidably supported on the staple former 254 and located between the side flanges 320. The compression coil spring 262 normally biases the staple holder 252 distally relative to the staple former 254 with the depending prong 260 biased against the distal end of the elongated central slot 256. The staple holder 252 and the staple 254 are inserted into the staple cartridge 240 between the lower upstanding flanges 292. The staple former 254 is slidably supported on the ledges 298 formed on the inside of the flanges 292. An ejector arm 322 extending from the distal end of the staple holder 252 has a notch 324 for receiving the dimpled portion 67 of the staple 65. A pusher finger 326 projects forwardly into the notch 324 at the distal end of the staple holder 252 for engaging the dimpled portion 67 of the staple 65 as the staple holder 252 is advanced to move the staple 65 into engagement with the anvil 250. The distal end of the ejector arm 322 is slanted away from the level of the pusher finger 326 and serves to disengage the staple 65 from the anvil 250 as the staple holder 252 is retracted after the staple 65 is formed. A pair of fingers 328 at the tip of the ejector arm 322 are spaced apart to receive the depending tab 308 therebetween.

The anvil 250 includes a pair of laterally spaced prongs 330 at its distal end which allow the ejector arm 322 to pass therebetween when the staple holder 252 is advanced. Each prong 330 includes an inclined ramp 332 for guiding the crown 66 of the staple 65 into engagement with the proximal side of the prong 330.

The staple follower 264 is channel-shaped and includes a generally flat top portion 340 which is slidably received between the lower flanges 292 and the upper flanges 296. The staple follower 264 also has a pair of depending side flanges 342 on its opposite sides which are received in the channels 294 adjacent to the lower flanges 292. The staple follower 264 includes a rearwardly projecting post 344 which is inserted into the distal end of the compression coil spring 266.

Figure 19:
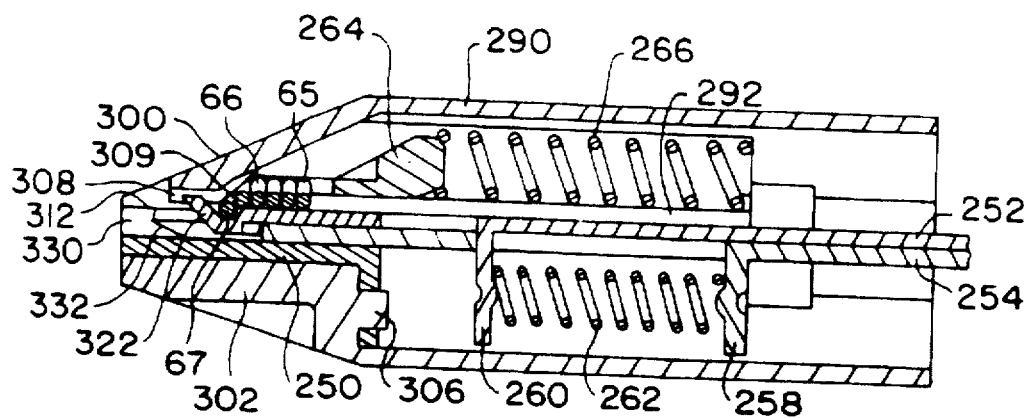
FIG. 19 is an enlarged longitudinal section of the staple cartridge of FIG. 9 showing the staple forming mechanism in a retracted position.

Referring to FIGS. 9 and 19, a stack of staples 65 is mounted in the staple cartridge housing 240 with the staple crowns 66 resting on and slidably supported by the elongated flanges or guide rails 292. The dimpled portions 67 of the staples 65 rest on top of the staple holder 252. The row of staples 65 is urged forwardly toward the distal end of the cartridge 240 by the staple follower 264 and the compression coil spring 266. The staple former 254 is biased rearwardly by the return spring 174 (FIG. 2) in the actuator handle assembly 80 to urge the depending prong 258 against the front of the retainer 242. The staple holder 252 is biased forwardly by the compression coil spring 262 which urges the depending prong 260 against the front edge of the slot 256 in the staple former 254. The ejector arm 322 at the distal end of the staple holder 252 is located adjacent to the guide tab 308 at the front of the tapered nose 300 of the staple cartridge 240.

As shown in FIG. 19, the offset or dimpled portion 67 of the forwardmost staple 65 is located at a level different from the remaining staples 65 in the stack. The dimpled portion 67 of the forwardmost staple 65 is received in the notch 324 in front of the pusher finger 326. When the staple holder 252 is advanced, the dimpled portion 67 of the forwardmost staple 65 is advanced along the sloped surface 309 and adjacent to the guide tab 308 by the pusher finger 326. The top portion or crown 66 of the forwardmost staple 65 is advanced along a path between the inclined ramps 310 (FIG. 14) and the inclined ledges 293 of the guide rails 292 to rotate the staple 65 by 90 degrees about its dimpled portion 67.

Figure 20:
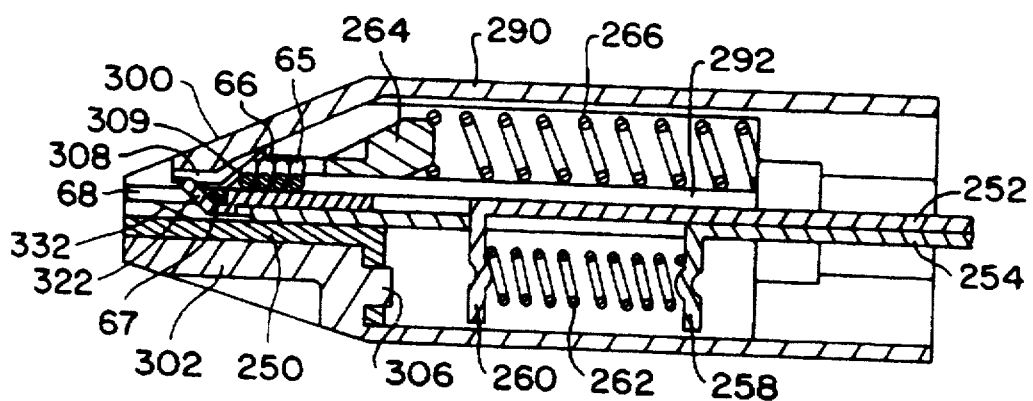
FIG. 20 is an enlarged longitudinal section of the staple cartridge of FIG. 9 showing the staple forming mechanism advanced to rotate a staple into a longitudinal orientation.
Figure 21:
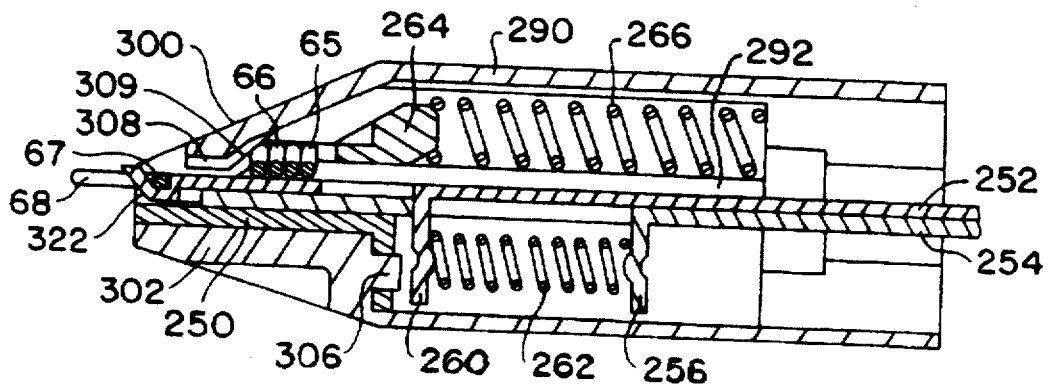
FIG. 21 is an enlarged longitudinal section of the staple cartridge of FIG. 9 showing the staple forming mechanism advanced to clamp the staple against an anvil of the staple cartridge.

As shown in FIG. 20, with the staple holder partially advanced, the forwardmost staple 65 is rotated into a longitudinal orientation with its staple legs 68 parallel to the longitudinal axis of the staple cartridge housing 240. Thereafter, as shown in FIG. 21, when the staple holder 252 is fully advanced, the forwardmost staple 65 travels along the extensions 294 of the guide rails 292 and is clamped against the anvil prongs 330 with the staple legs 68 projecting distally from the front of the staple cartridge housing 240. The remaining staples 65 in the stack are restrained by the top of the staple holder 252 which engages the dimpled portions 67 of the staples 65.

The staple forming mechanism of the staple cartridge 100 is actuated by squeezing the staple actuating lever 88 toward the handle grip 86. As a result, the staple actuating lever 88 is pivoted about the pivot pin 96 and the upright fingers 170 advance the slide member 154 in the distal direction. The slide member 154 advances the staple driver 76 in the distal direction which, in turn, advances the plunger 270 to actuate the staple holder 252 and the staple former 254. After the staple holder 252 and the staple former 254 are fully advanced to form one of the staples 65, the staple actuating lever 88 is released and returned to its original position by the return coil spring 174, which retracts the slide block 154 and the staple driver 76.

Figure 22:
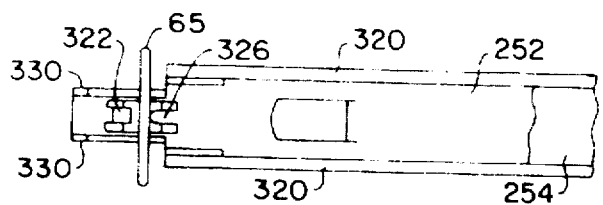
FIGS. 22–26 illustrate the operation of the staple forming mechanism in advancing and forming a staple.

The operation of the staple forming mechanism is illustrated in FIGS. 22-26 which, for clarity, show only one staple 65. FIG. 22 shows the staple 65 positioned in the notch 324 in front of the pusher finger 326 at the start of the staple forming cycle which corresponds to the position of the staple holder 252 and staple former 254 shown in FIG. 19. Initially, when the staple actuating lever 88 is actuated, the staple holder 252 and the staple former 254 are advanced simultaneously to advance the staple 65 toward the prongs 330 of the anvil 250. As the staple 65 is advanced toward the anvil prongs 330, the staple 65 is rotated by 90 degrees into a longitudinal orientation (FIG. 20) with the staple legs 68 pointing distally.

Figure 23:
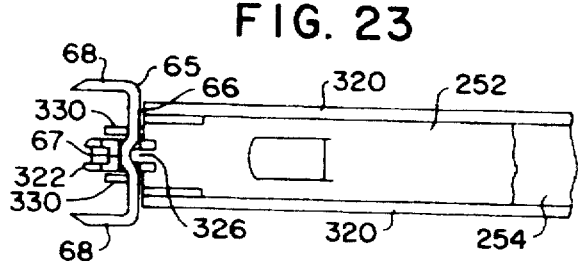

FIG. 23 shows the staple holder 252 and the staple former 254 advanced to a staple clamping position corresponding to FIG. 21 in which the staple crown 66 is clamped between the pusher finger 326 and the prongs 330 of the anvil 250. Thereafter, as the staple actuating lever 88 is actuated, only the staple former 254 is advanced while the staple holder 252 remains stationary with the staple 65 clamped against the anvil prongs 330.

Figure 24:
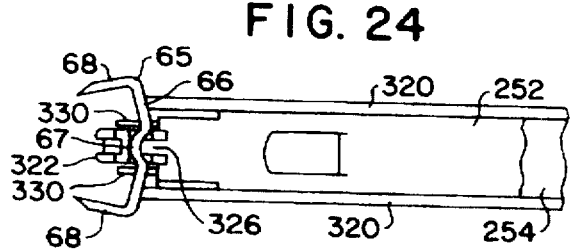

FIG. 24 shows the initial movement of the staple former 254 relative to the staple holder 252 to form the staple 65 about the anvil prongs 330. The initial contact of the former flanges 320 with the staple 65 results in a slight bending of the staple crown 66 with the staple legs 68 angled toward each other.

Figure 25:
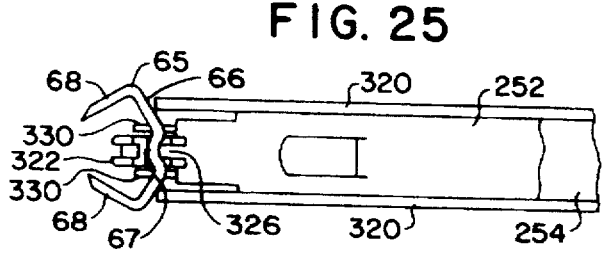
Figure 26:
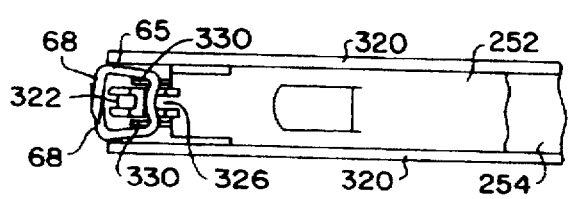

FIG. 25 shows an intermediate stage of the staple forming cycle in which the former flanges 320 are further advanced to bend the staple crown 66 around the anvil prongs 330 to bring the staple legs 68 closer together. FIG. 26 shows the final stage of the staple forming cycle in which the former flanges 320 are fully advanced to bend the staple legs 68 into an overlapping configuration to secure the staple 65 to the tissue.

After the staple 65 is completely formed, the staple actuating lever 88 is released and the staple former 254 is moved rearwardly relative to the staple holder 252 by the compression coil spring 262. When the depending lug 260 is engaged by the front edge of the slot 256, the staple holder 252 and the staple former 254 are retracted together by the return spring 174 in the actuator handle assembly 80. The ejector arm 322 lifts the formed staple 65 from the anvil prongs 330 as the staple holder 252 is retracted. The staple holder 252 and the staple former 254 are returned to the start position shown in FIG. 19 where the next staple 65 is received in the notch 324 in front of the pusher finger 326. Then, the staple forming cycle is repeated to form the next staple 65.

The actuator handle assembly 80 includes a precock ratchet mechanism comprising the ratchet spring 178 and the ratchets 182 which prevents the retraction of the staple forming mechanism until the staple 65 is completely formed. The operation of the ratchet mechanism is illustrated in FIGS. 27-31 which show the various ratchet positions corresponding to the stages of the staple forming cycle shown in FIGS. 22-26, respectively.

Figure 27:
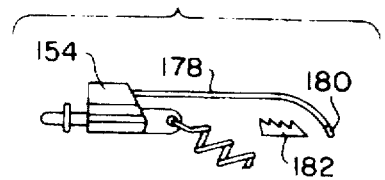
FIGS. 27–31 are fragmentary views showing the operation of a precock ratchet mechanism in the actuator handle assembly.
Figure 28:
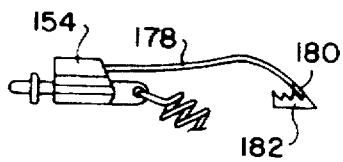

As shown in FIG. 27, each spring arm 180 of the ratchet spring 178 is initially disengaged from each ratchet 182 with the staple holder 252 and the staple former 254 located in the retracted position (FIG. 22). As shown in FIG. 28, each spring arm 180 of the ratchet spring 178 is engaged in the first notch of each ratchet 182 with the staple holder 252 and the staple former 254 in the advanced position (FIG. 23) in which the staple 65 is clamped against the anvil prongs 330. Thereafter, the engagement of the ratchet spring arms 180 with the ratchets 182 prevents the staple holder 252 and the staple former 254 from being retracted until the staple forming cycle is completed.

Figure 29:
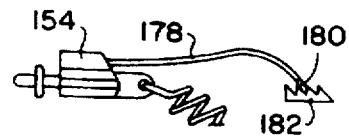
Figure 30:
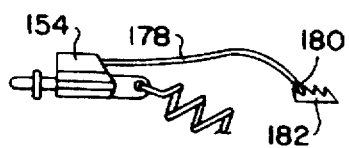

As shown in FIG. 29, each spring arm 180 of the ratchet spring 178 is engaged in the second notch of each ratchet 182 with the flanges 320 of the staple former 254 initially engaged with the staple crown 66 to begin the forming of the staple 65 (FIG. 24). As shown in FIG. 30, each spring arm 180 of the ratchet spring 178 is engaged in the third notch of each ratchet 182 with the former flanges 320 advanced to the intermediate stage of the staple forming cycle (FIG. 25) in which the staple legs 68 are partially closed.

Figure 31:
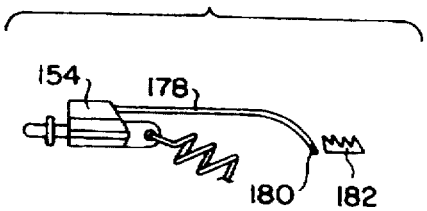
Figure 37:
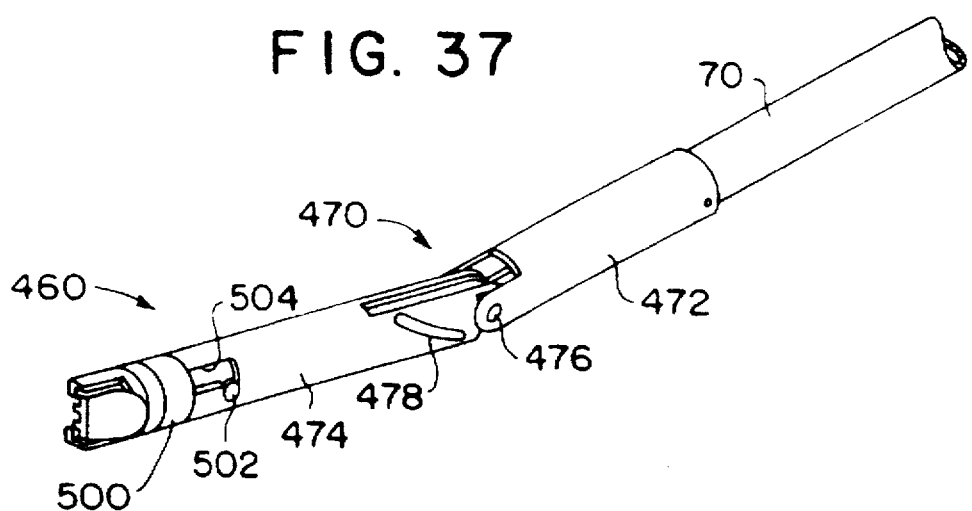
FIG. 37 is a perspective view of another embodiment of a stapling head assembly for use with the surgical stapling instrument of this invention.
Figure 38:
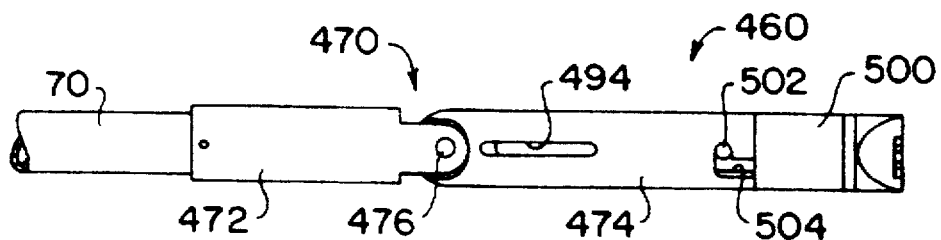
FIG. 38 is a side view of the stapling head assembly from the opposite side of FIG. 37.

As shown in FIG. 31, each spring arm 180 of the ratchet spring 178 is disengaged from each ratchet 182 with the former flanges 320 fully advanced (FIG. 26) to bend the staple legs 68 into an overlapping relationship. Each spring arm 180 travels rearwardly adjacent to the unnotched side of the corresponding ratchet 182 to allow the ratchet spring 178 to return to its retracted position (FIG. 27) when the staple actuating lever 88 is released.

In performing a hernia repair procedure, the endoscopic surgical stapling instrument 50 is inserted into a body cavity through a trocar tube or cannula installed in a body wall. Initially, the surgical stapling instrument 50 is introduced into the body cavity in its non-articulated mode, i.e., with the staple cartridge 100 aligned with the longitudinal axis of the support tube 70. An endoscope may be inserted into the body cavity through a separate trocar tube or cannula for observation of the surgical site. The stapling cartridge 100 is positioned in the desired orientation over the surgical site by operating the rotatable adjusting knob 82 and the saddle-shaped actuator 84 to adjust the rotational orientation of the support tube 70 and the angular orientation of the staple cartridge 100. The staple cartridge 100 can be articulated to angles of 15, 30, 45 and 60 degrees relative to the support tube 70 by retracting the saddle-shaped actuator 84.

If it is desired to change the rotational orientation of the staple cartridge 100 on its axis, the staple cartridge 100 is returned to the non-articulated mode by sliding the saddle-shaped actuator 84 forwardly. The surgical stapling instrument 50 is withdrawn from the trocar tube or cannula and the staple cartridge 100 is rotated manually relative to the support tube 70. Then, the surgical stapling instrument 50 is reintroduced into the body cavity in its non-articulated mode and the orientation of the staple cartridge 100 is adjusted by operating the rotatable adjusting knob 82 and the saddle-shaped actuator 84.

With the staple cartridge 100 adjusted to the desired orientation, the staple actuator lever 88 is squeezed to actuate the staple forming mechanism in the staple cartridge 100 to fasten one of the staples 65 to the tissue at the surgical site. Thereafter, the staple cartridge 100 is shifted to another location and the operation is repeated to fasten another staple 65 to the tissue. When the staple actuator lever 88 is released, the formed staple 65 is disengaged from the anvil 250 of the staple cartridge 100.

Referring to FIG. 18, the surgical stapling instrument 50 can be used to secure a hernia patch 62 at a desired surgical site. The hernia patch 62 is attached to internal body tissue 64 by applying a series of staples 65 to the edges of the hernia patch 62. The staple cartridge 100 is readily adjustable into the different orientations to apply the staples 65 at various locations along the edges of the hernia patch 62.

FIGS. 32 and 33 illustrate an alternative embodiment of the surgical stapling instrument, generally 350, including a distal stapling head assembly 360 which is pivotally connected to an elongated support tube 370 rotatably mounted on a proximal actuator handle assembly 380. A rotatable adjusting knob 382 is mounted at the distal end of the actuator handle assembly 380 for rotating the support tube 370 about its longitudinal axis. A saddle-shaped actuator 384 is slidably mounted on the actuator handle assembly 380 for controlling the pivotal movement of the stapling head assembly 360 relative to the support tube 370. The actuator handle assembly 380 has a depending handle grip 386 and a pivotally mounted staple actuating lever 388 for actuating the stapling head assembly 360. The internal components of the stapling head assembly 360, the support shaft 370 and the actuator handle assembly 380 are substantially identical to the corresponding components of the surgical stapling instrument 50 described above. Accordingly, no detailed description of the internal components of the surgical stapling instrument 350 is necessary, and it will be understood by persons skilled in the art that the previous description of the internal components of the surgical stapling instrument 50 is applicable to the internal components of the surgical stapling instrument 350, unless otherwise described.

The stapling head assembly 360 includes a rotatably mounted staple cartridge 400 which is substantially identical in construction to the stapling cartridge 100 described above. The stapling head assembly 360 is pivotally mounted on the support tube 370 by a pivot connection 390 which is substantially identical to the pivot connection 200 described above.

As shown in FIG. 33, the handle assembly 380 includes a pair of hollow handle sections 392 which are adapted to snap fit together. Each of the handle sections 392 includes a distally extending elongated, semi-cylindrical neck portion 394 in which the proximal end of the support tube 370 is received and mounted for rotation about its longitudinal axis relative to the handle assembly 380. Each of the handle sections 392 includes an internal annular flange 395 (one shown) for engaging a radially projecting flange 372 at the proximal end of the support tube 370 to retain the support tube 370 within the handle assembly 380. The staple actuating lever 388 is pivotally mounted on the actuator handle assembly 380 by a pivot pin 396.

As shown in FIGS. 32 and 33, the adjusting knob 382 comprises a pair of elongated, hollow tapered sleeve-like sections 402 which fit together over the neck portions 394 of the handle sections 392. Each of the sleeve-like knob sections 402 has an inwardly projecting prong 403 adjacent to its distal end. The prongs 403 are received in a pair of holes formed on opposite sides of the support tube 370 to secure the knob sections 402 to the support tube 370. The actuator handle assembly 380 and the adjusting knob 382 include the same ratchet mechanism, described above in connection with the stapling instrument 50, which allows the adjusting knob 382 to rotate the support shaft 370 about its longitudinal axis in sixteen equal intervals of 22½ degrees. Each of the knob sections 402 has an enlarged rear section 407 provided with alternating longitudinal ridges 408 and finger receiving grooves 409 which facilitate the rotation of the adjusting knob 382 and the support tube 370 by the surgeon.

The actuator handle assembly 380 includes a rotatable control knob 410 for controlling the rotation of the staple cartridge 400 about its longitudinal axis relative to the support shaft 370. The control knob 410 includes an elongated hollow, conically tapered portion 412 which is rotatably received between the sleeve-like sections 402 of the adjusting knot 382 and the cylindrical neck portions 394 of the handle sections 392. A hollow cylindrical, internally toothed geneva gear wheel 414 is secured within the distal end of the conically tapered body 412 for rotation with the control knob 410. A first pinion gear 416 which is rotatably mounted on the inside of the support tube 370 extends through a window 372 (FIG. 35) formed in the side of the support tube 370 and engages the internal teeth on the geneva gear wheel 414. The pinion gear 416 is attached to a flexible cable 418 which extends longitudinally through the support shaft 370 and the pivot connection 390. The distal end of the flexible cable 418 is connected to a second pinion gear 420 rotatably supported in a bushing 422 (FIG. 34) mounted on the inside of one of the clamshell members 424 forming part of the pivot connection 390. The flexible cable 418 is formed of conventional materials such as steel alloys. The staple cartridge 400 is mounted on a cylindrical retainer 426 which is rotatably supported by the clamshell members 424 of the pivot connection 390. The cartridge retainer 422 has an internally toothed geneva gear wheel 428 (FIG. 36) at its proximal end which engages the pinion gear 420.

In the operation of the surgical stapling instrument 350, the control knob 410 is used to control the rotational orientation of the staple cartridge 400 relative to the support shaft 370 and the pivot connection 390. The rotation of the control knob 410 is transmitted via the flexible cable 418 to the cartridge retainer 422 which rotates the staple cartridge 400 about its axis. As a result, the rotational orientation of the staple cartridge 400 relative to the support shaft 370 is adjustable by the rotation of the control knob 410.

Except for the control knob 410 which rotates the staple cartridge 400, the surgical stapling instrument 350 operates in substantially the same manner as the stapling instrument 50 described above. The rotatable adjusting knob 382 is used to rotate the support shaft 370 relative to the actuator handle assembly 380. The saddle-shaped actuator 384 is slidable longitudinally along the actuator handle assembly 380 to pivot the stapling head assembly 360 about an axis transverse to the longitudinal axis of the support shaft 370. The staple actuating lever 388 is pivoted to actuate the staple forming mechanism of the staple cartridge 400 in substantially the same manner as described above.

Figure 48:
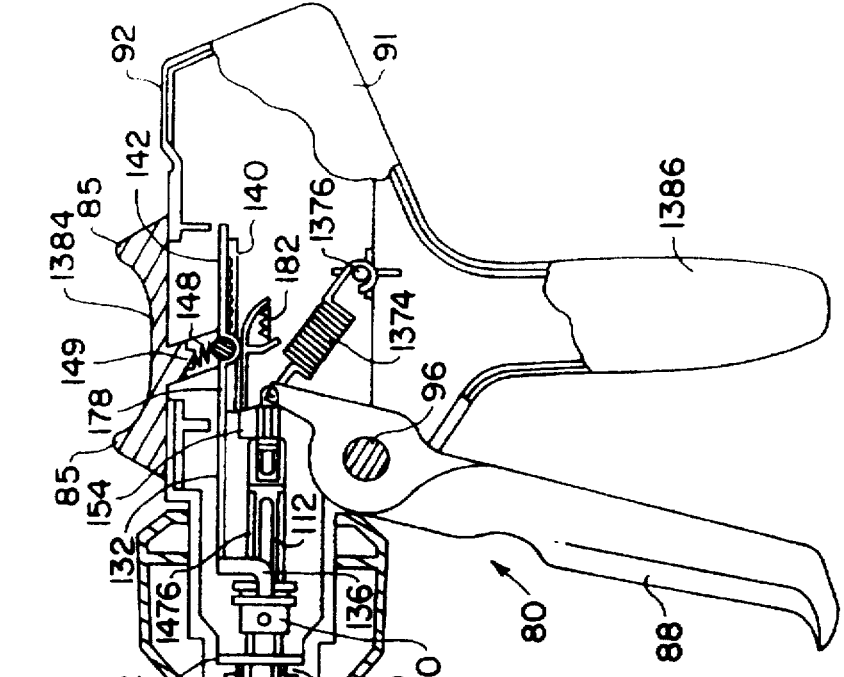
FIG. 48 is a further modification of the assembly of FIGS. 34-36.
Figure 50:
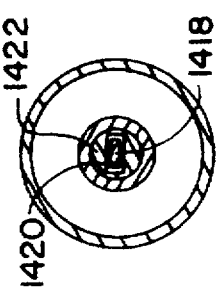
FIG. 50 is a cross sectional view taken along lines 50—50 of FIG. 48.
Figure 49:
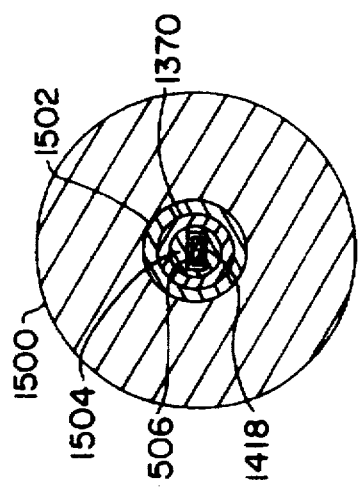
FIG. 49 is a cross sectional view taken along lines 49—49 of FIG. 48.

FIGS. 48–50 show an embodiment which combines the rotating and articulating features of the embodiment of FIGS. 2 and 33, wherein these features are accomplished by the same mechanism. All elements of FIG. 48 corresponding to those of FIG. 2 are similarly numbered and, except as hereinafter provided, function identically to the corresponding elements as described in reference to FIG. 2. Now, the gears and flexible cable contained in the embodiment of FIG. 33 have been replaced by a centrally disposed metal band 1418. This metal band 1418 is preferably formed of a memory metal, such as nitinol, which is able to both operate the staple driver and articulate and rotate the cartridge 1400.

The bank 1418 passes through a hole 1420 in the center of a plate 1422 within the staple cartridge 1400. The band 1418 is connected at its distal end to a staple driver 1476. The band 1418 is connected at its proximal end to the articulation saddle 1384. The band 1418 is also connected at its proximal end to the handle 1386 via a spring 1374 and pin 1376 in handle 1386.

In the range of articulation of the staple cartridge 1400, band 1418 has an elastic memory. Thus, dependent on the relative slidable positioning of the band 1418 with respect to the staple cartridge 1400, the elastic memory of the band 1418 will cause the staple cartridge 1400 to articulate about the pivot 1236 with respect to the shaft 1370. However, the shaft 1370 is rigid enough that the band 1418 has little or no effect on its relative radical position in the shaft 1370. The band 1418 is long enough to be operable in a handle 1386 at any distal positioning of the band 1418 by the saddle 1384. Of course, rotation of shaft 1370 and cartridge 1400 together is possible, as explained above.

In the embodiment of FIG. 48, the staple cartridge 1400 preferably includes a series of detents, not illustrated, as previously described, for limiting the rotation of the staple cartridge 1400 to specific increments. This rotation is accomplished by use of a circular knob, generally 1500, that, similar to the knob 410 in the FIG. 33 embodiment, enables the rotation of the staple cartridge through rotation of a collar 1502 which is attached to the support tube 1370. The support tube 1370 in turn contains a plate 1504, illustrated in FIG. 49, having a rectangular-shaped hole 1506 therein for slidably receiving the memory metal band 1418 therethrough. Thus, when the knob 1500 is rotated, the support tube 1370 and plate 1504 are also rotated, thereby rotating the metal band 1418, which in turn rotates the plate 1422 in the staple cartridge, which in turn rotates the staple cartridge 1400. This, of course, is an optional method of rotating the cartridge 1400 since the external sleeves 601 and 602 could accomplish the same function, if they were used. Although these sleeves 601 and 602 are shown in the embodiment of FIG. 48, they could optionally be removed in view of the knob 1500 and its associated components for rotating the cartridge 1400.

The memory metal rod 1418 also cooperates with the staple driver mechanism 1476 substantially as described previously with respect to the embodiment of FIG. 2 for actuating the staple driving mechanism of the staple cartridge.

In operation, the band 1418 causes articulation (via its memory and operation of the saddle 1384) of the staple cartridge and operation (via its rigidity and operation of the handle 1386) of the staple driving function. Thus, in this embodiment, the one component, the band 1418, has substituted many moving parts in the instrument of FIGS. 2 and 33.

FIGS. 37-40 show an alternative embodiment of a stapling head assembly, generally 460, which can be used with the surgical stapling instrument 50 described above. The stapling head assembly 460 is pivotally mounted at the distal end of the support tube 70 by a pivot connection 470 including a tubular pivot housing 472 secured to the support tube 70 and a tubular cartridge support member 474 pivotally connected to the pivot housing 472 by a pair of pivot pins 476 extending laterally from opposite sides of the cartridge support member 474. An inclined slot 478 is formed on one side of the cartridge support member 474.

A staple cartridge 500 is mounted at the distal end of the cartridge support member 474. The staple cartridge 500 is generally cylindrical in shape and is adapted to be received in the open distal end of the cartridge support member 474. The staple cartridge 500 has a pair of latch pins 502 projecting radially outward its opposite sides. The latch pins 502 are received and latched in a pair of slots 504 extending longitudinally from the distal end of the cartridge support member 474. The latch pins 502 and slots 604 allow the staple cartridge 500 to be disengaged from the cartridge support-member 474 when it is-desired to replace the staple cartridge 500.

Figure 40:
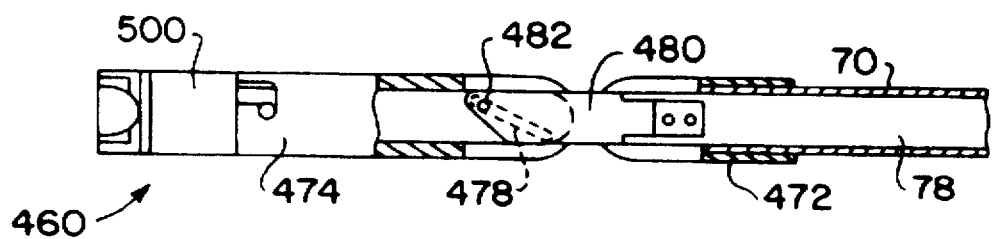
FIG. 40 is a partially cutaway side view of the stapling head assembly from the opposite side of FIG. 39.

As shown FIG. 40, an articulation control member 480 is slidably mounted in the pivot housing 472 and is connected to the articulation driver 78. A laterally projecting guide pin 482 is located adjacent to the distal end of the articulation control member 480 and is slidably received in the inclined slot 478 of the cartridge support member 474. The inclined slot 478 and the guide pin 482 convert longitudinal movement of the articulation driver 78 into pivotal movement of the stapling head assembly 460 about the pivot pins 476.

Figure 39:
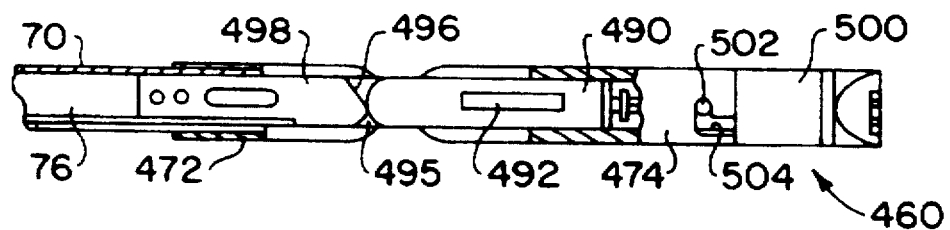
FIG. 39 is a partially cutaway side view of the stapling head assembly of FIG. 38.

As shown in FIG. 39, a plunger 490 is slidably mounted for longitudinal movement in the cartridge support member 474. The plunger 490 includes an elongated laterally projecting side flange 492 which is slidably received in a longitudinal slot 494 (FIG. 38) formed on the side of the cartridge support member 474. The plunger 490 has a semi-circular rear edge 495 which is engaged by an inclined cam surface 496 on a drive member 498 mounted at the distal end of the staple driver 76. The front end of the plunger 490 is engaged with the staple forming mechanism inside the staple cartridge 600.

When the staple driver 76 is advanced in the distal direction, the plunger 490 is advanced to actuate the staple forming mechanism of the staple cartridge 600 which operates in substantially the same manner as described above. The semi-circular rear edge 496 of the plunger 90 and the inclined cam surface 498 at the distal end of the staple driver 76 allow the staple forming mechanism to be actuated in any angular orientation of the staple cartridge 600.

Another highly preferred embodiment of the invention is illustrated in FIGS. 44-47. In this embodiment, an improved device, generally 700, for pivoting, or articulating the staple cartridge 100 with respect to the support tube 70 is illustrated. The device includes a control knob 702 rotatably mounted on the support shaft 70 proximate the handle assembly 80. The control knob 702 is preferably mounted to the support shaft 70 and rotates about an axis A4 generally perpendicular to the longitudinal axis A1 of the support shaft 70.

The control knob 702 is adapted for transferring rotational motion of the control knob to an articulation driver assembly, generally 704, in a longitudinal direction generally parallel to the longitudinal axis A1 of the support shaft 70. Preferably, the articulation driver assembly comprises a sleeve 705 rotatably positioned on the support shaft 70. The sleeve 705 has an annular channel 706 therein. As illustrated in FIGS. 44-47, the shaft 70 slidably receives a pair of rods 707. Each of the rods 707 has a flange 707a extending perpendicularly from the proximal end of the rod 707. Each flange 707a in turn passes through and rides along a pair of slots 708 on either side of the shaft 70, the slots 708 preferably being oriented generally parallel to and coplanar with the axis A1 of the shaft 70. The flanges 707a also ride within the annular channel 706 of the sleeve 705. As illustrated in FIGS. 44-47, each of the rods 707 may slidably ride within a guide 730 inside the tube 70 for maintaining spacing between the rods 707 and walls of the tube 70.

Referring again to FIG. 44, the control knob 702 preferably includes a worm gear 712 about the control knob axes A4 for transferring rotational motion about the control knob axis A4 to rotational motion about the support shaft longitudinal axis A1. This is preferably accomplished with an annular gear 713 fastened to the sleeve 705.

Figure 46:
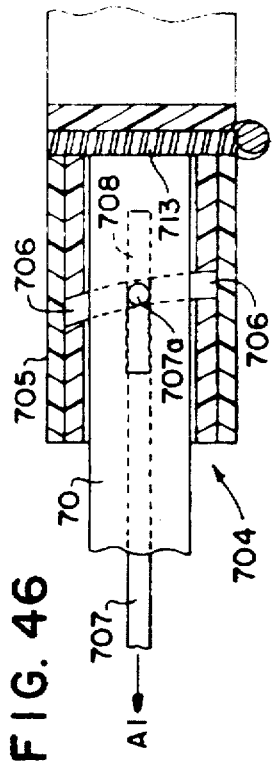
FIG. 46 is a cross sectional, elevational plan view of the articulation device of FIG. 44, taken along line 46—46.

As further illustrated in FIG. 46, the annular channel 706 of the sleeve 705 has in inclined orientation with respect to the longitudinal axis A1 of the support shaft 70. This inclined orientation converts the rotational motion of the sleeve 705 and annular channel 706 to the longitudinal motion of the flange 707a within the slot 708 when the sleeve 705 is rotated.

Figure 47:
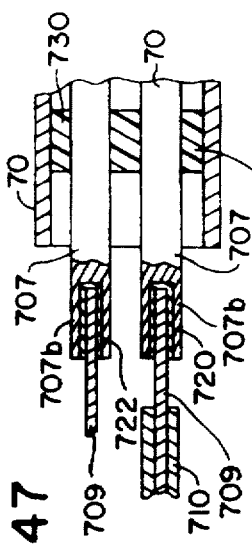
FIG. 47 is a partial cross sectional, partial cutaway view of the encircled portion of the device of FIG. 45.
Figure 45:
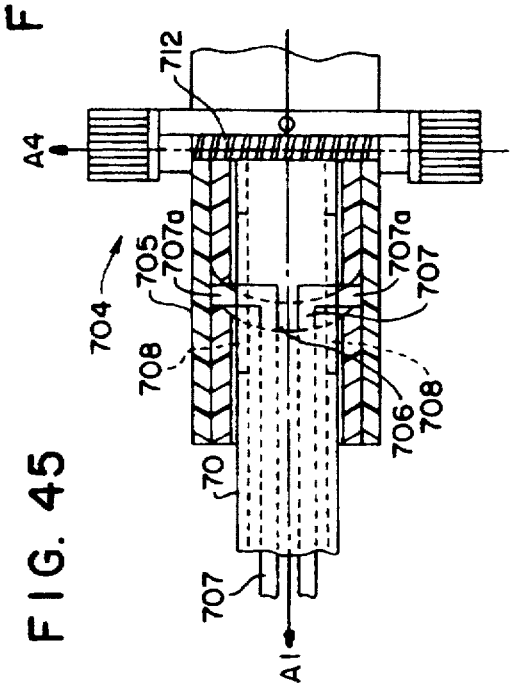
FIG. 45 is a cross sectional, top plan view of the articulation device of FIG. 44, taken along line 45—45.

As best seen in FIG. 47, each rod 707 has connected to its distal end 707b a flexible cable 709 which may be pushed and pulled by the rod 707 as its flange 707a slides in the slot 708 and as the rod 707 slides in the support tube 70. Preferably, each rod end 707b has a blind hole 720, which receives the cable 709 as illustrated in FIG. 47. As illustrated, the cable 709 is slipped into the blind hole 720 and secured to the rod 707, for example, with a crimp or an adhesive material 722. Each flexible cable 709 is connected at its distal end to the stapling head assembly 60 as illustrated. In making this connection, the cable 709 is fed through the hollow support tube 70, through the pivot connection 200 and attached to the stapler head assembly 60 at a point in the plane formed by the intersection of the axes and A1 and A3, but at a point spaced from the axis A3. Preferably, this connection between the cable 709 and the stapler head assembly 60 is achieved by passing the cable 709 into a hole or bore in the stapler head assembly 60, and fastening the end of the cable to the assembly 60 with an adhesive or any other acceptable fastening method.

In a highly preferred embodiment of the invention illustrated in FIG. 47, the flexible cables 709 are slidably received within a flexible sleeve 710, which provides reduced friction as the cable 709 is pushed and/or pulled through the support tube 70. Preferably, the flexible sleeves 710 are fixed with respect to the support tube 70, allowing slidable motion of the cables 709 therein, for example, by attaching the ends of the flexible sleeves 710 to the support tube 70. The flexible sleeves 710 are preferably fabricated of fiberglass reinforced or steel reinforced nylon, Teflon®, polyethylene, among other equivalent materials known in the art.

Figure 44:
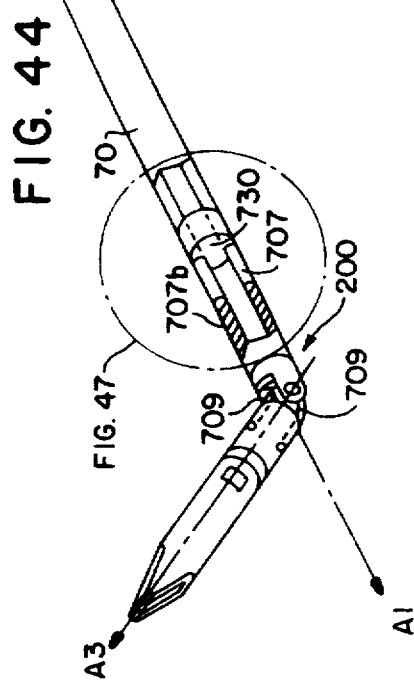
FIG. 44 is a perspective view of an improved stapling instrument and articulation device of the present invention.

The embodiment illustrated in FIGS. 44-47 is a "push/pull" system. That is, when one of the cables 709 is in compression, the other cable 709 is in tension as dictated by the rotation of the sleeve 705. As illustrated in FIG. 44, the length of the cable 709 is relatively short with respect to the length of the support shaft 70 and rods 707, enabling each cable 709 to be pushed without buckling substantially. Buckling is further avoided by the use of the flexible sleeves 710.

In addition to a "push/pull" system, it would also be possible to arrange the embodiment of FIGS. 44-47 in either a "pull/pull" or a "push/push" system, whereby both cables are simultaneously pulled or pushed, respectively.

The flexible cables 709 may be fabricated of any materials suited for the purpose including, by way of example, but not limitation, steel, nitinol, nylon, and fiberglass, manufactured by Hoechest Celanese. The flexible cable 709 preferably is flexible and retains good flexing memory.

The articulation assembly 700 of the invention offers several advantages with respect to prior articulation devices. The assembly 700 allows a complete sweep of articulation over the entire range of articulation (generally 0°-60°), rather than the more limited fixed angles of articulation provided with the prior ratchetting mechanism. Additionally, because of the use of the worm gear mechanism, with its advantageous gear ratios, preferably greater than 2:1 to prevent back-driving, the degree of articulation is both precisely and easily controlled with the turn of the control knob 702.

The devices for providing articulation and rotation to the tip of a shaft previously described can be employed in a wide variety of surgical instruments other than stapling devices. For example, since the support tube 70 is hollow, it may contain a number of other surgical apparatus, including cameras, illumination devices, ligation devices, forceps, drilling devices, suction devices, insufflation devices, cutting devices, scalpels, clamps, absorption devices, injection devices, drainage devices, lasers, cryogenic devices, sonic devices, e.g., for providing sonar detection of blood vessels, illumination devices, such as fiber optic cable, and surgical stitching devices. The device of the present invention allows such surgical apparatus to be inserted into a patient through a cannula, such as previously described, and articulated and/or rotated to the point of interest within the patient.

Figure 51:
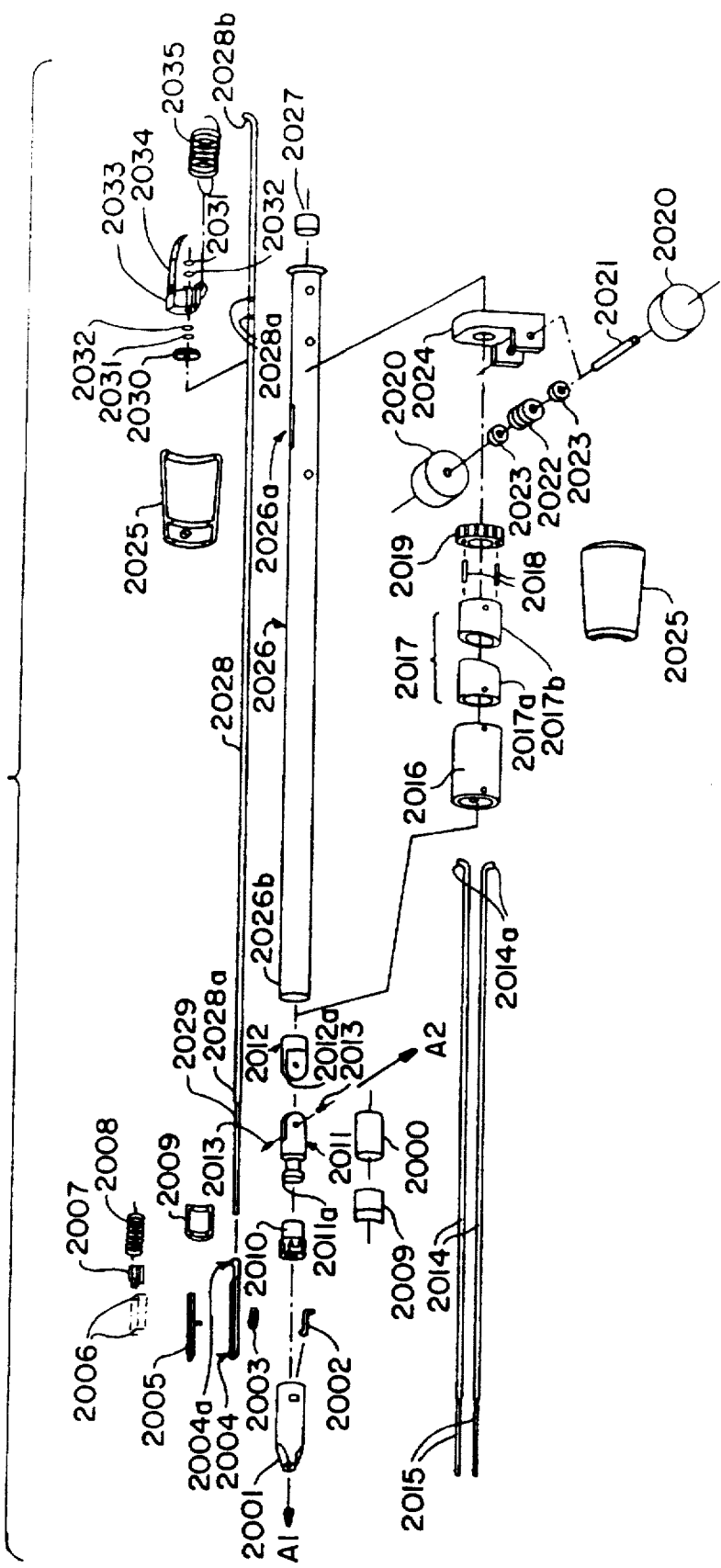
FIG. 51 is an exploded isometric view of the front portion of a highly preferred stapling instrument of the invention.
Figure 51A:
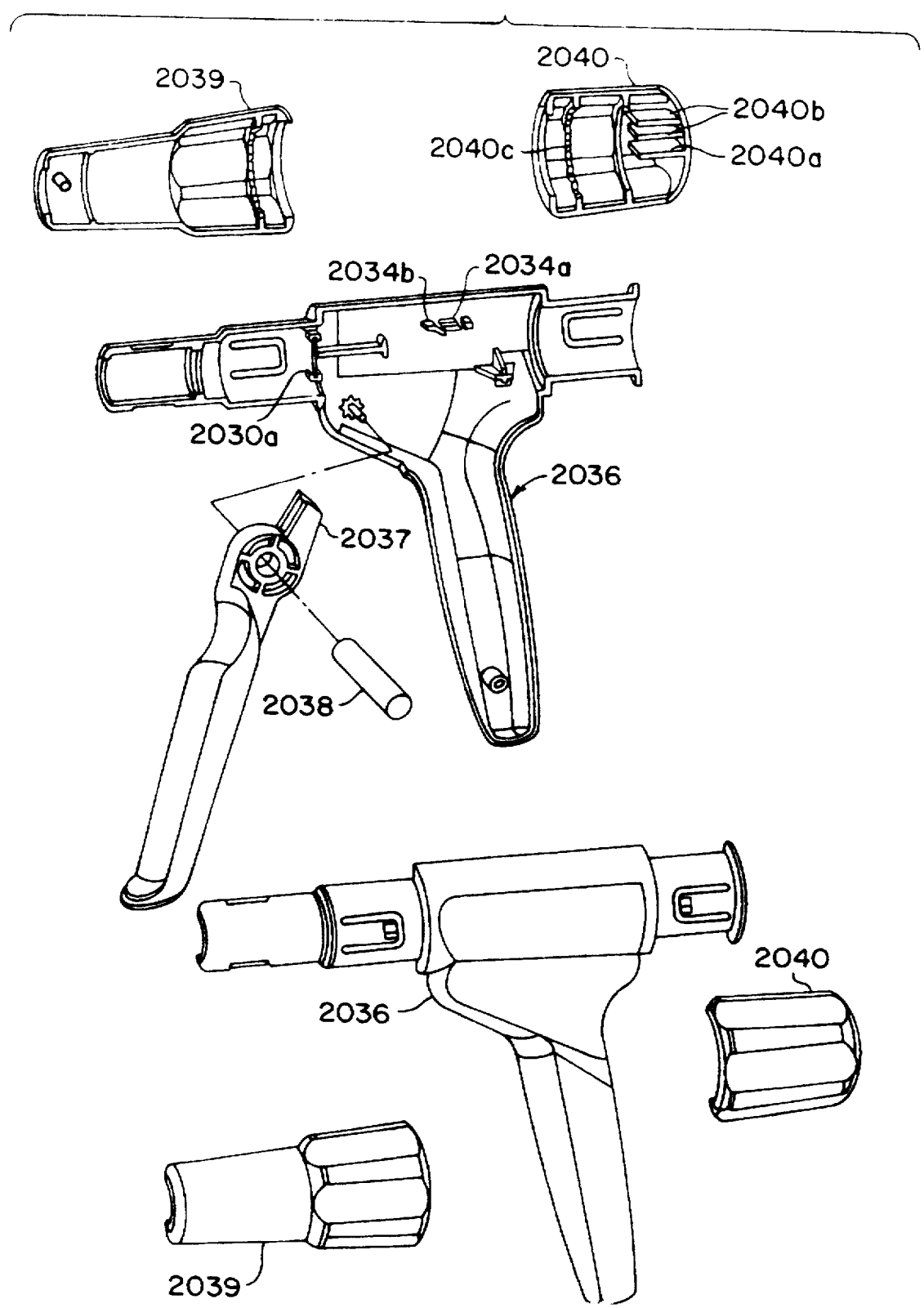
FIG. 51a is an isometric exploded view of the handle portion of the instrument illustrated in FIG. 51.
Figure 52:
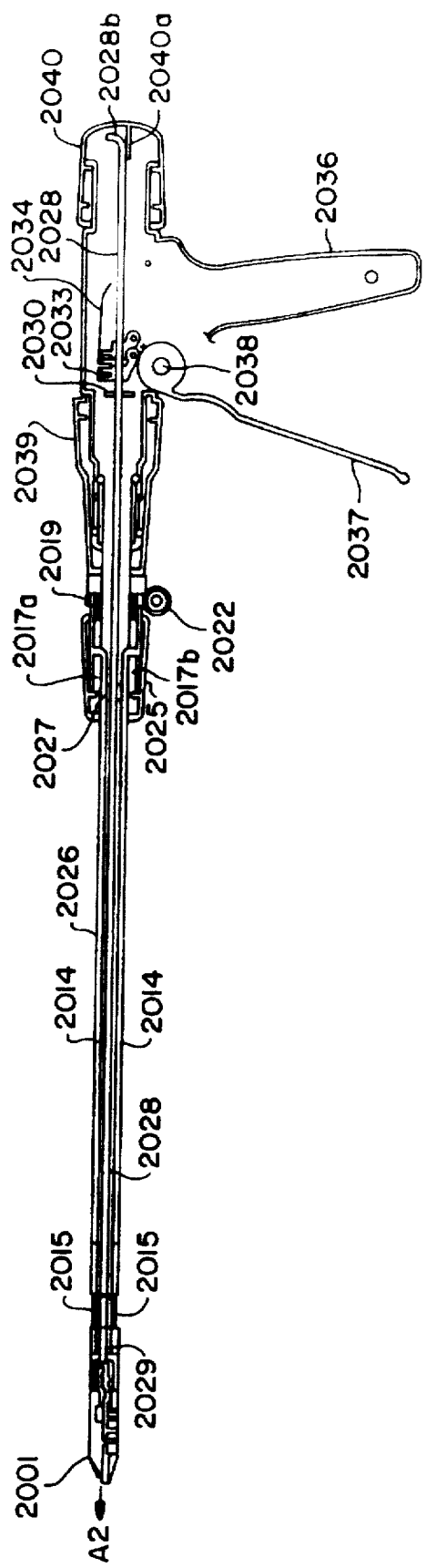

Referring now to FIGS. 51, 51a, and 52, there is illustrated yet another highly preferred embodiment of the invention. As illustrated in this embodiment, a staple cartridge 2001 includes an anvil 2002, a staple holder 2005, and a staple former 2004 preferably made of stainless steel and functioning as previously described. A compression coil spring 2003 biases the staple holder 2005 away from the staple former 2004, also as previously described. A feeder shoe 2007 is slideably mounted within the staple cartridge 2001 for urging a series of staples 2006 toward the distal end of the cartridge 2001. The feeder shoe 2007 is biased in the distal direction by a compression coil spring 2008 which is mounted on a cartridge retainer 2010 substantially as previously described.

In the embodiment of FIG. 51, the staples 2006 are driven with a modified staple driver comprising a rod 2028 having fastened at its distal end 2028c a flexible member 2029. This flexible member 2029 in turn is fastened at its distal end to the staple former 2004, for example, by being crimped at location 2004a in the staple former 2004. In forming the staples 2006, the staple driver rod 2028 is pushed through the support tube 2026, thereby driving the flexible member, 2029, which is stiff enough to drive the staple former 2004 toward the distal end of the staple cartridge 2001, forming the staples around the anvil 2002. This staple forming procedure is substantially the same as previously described herein with the exception of the modified staple driver 2028, 2029, 2004. This modified staple driver replaces the plunger 270 and staple driver 76 previously described.

In order to actuate the staple driver rod 2028, the rod preferably is actuated by a trigger mechanism 2037 pivotally supported on a handle 2036 with a pin 2038 as illustrated in FIG. 51a and 52. The trigger mechanism 2037 is biased in an open or disengaged position by a coil spring 2035 in tension. This trigger mechanism 2037, spring 2035, and handle 2036 (held between halves 2039) are assembled in substantially the same way as like components illustrated in FIG. 52.

The staple driver rod 2028 is rotatably captured by a link 2033 in combination with a series of washers 2032 and snap rings 2031 as illustrated. The snap rings 2031 snap into annular grooves 2028a on the staple driver rod 2028. The link 2033 is retained by the spring 2035 and driven by the trigger 2037 as previously described.

As the trigger 2037 is pulled toward the handle 2036, the link 2033 forces the staple driver rod 2028 toward the distal end of the staple cartridge 2001, thereby driving the staple 2006. FIG. 52 illustrates the link 2033 in both the retracted and firing positions. The driver link 2033 further includes a projecting metal leaf spring 2034 curved downwardly at its proximal end for engaging a series of ratchets 2034a as previously described. The leaf spring 2034 and ratchets 2034a prevent the driver rod 2028 from reversing direction (i.e., toward the proximal end of the stapling instrument) until the stapling mechanism has gone through a complete stapling cycle by firing and forming a staple. This is accomplished with a ramp 2034b which allows the metal leaf spring 2034 to return to the beginning of the series of ratchets as the trigger 2037 is released and again biased in the open position by the spring 2035 after a complete fire of the staple 2006.

The staple driver rod 2028 also operates as a torque transmission mechanism for rotating the staple cartridge 2001 at any angle of articulation, as will now be described.

The rod 2028 is rotatably positioned within the support shaft 2026, and is preferably supported by a spacer 2027 and/or a guide 2030 to maintain a space between the rod 2028 and the inner walls of the support tube 2026. The guide 2030 preferably is trapped within a series of grooved flanges 2030a within the handle 2036 or support shaft 2026.

The rod 2028 includes at its proximal end a flange 2028b, which may simply be a "J-hook" bend in the rod 2028, which is captured by a knob 2040, which is externally and rotatably positioned on the handle apparatus 2036. This knob 2040 may comprise two clam shell halves, each of which may include a shelf 2040a on which the flange 2028b rides. Each side of the clam shell-type knob 2040 preferably includes one or more capturing flanges 2040b which trap the J-hook 2028b and allow the rod 2028 to be rotated when torque is applied to the external knob 2040. The shelf 2040a and capture flanges 2040b also allow the rod 2028 and J-hook 2028b to slide back and forth in response to a staple driving cycle, while retaining the J-hook 2028b within the space defined by the shelf 2040a and capture flanges 2040b.

The knob 2040 also preferably includes detents 2040c which allow the knob 2040 to provide incremental rotation to the staple cartridge 2001, in a manner substantially the same as previously described.

Accordingly, when the knob 2040 is rotated, the rod 2028 rotates in the same direction as does the flexible member 2029, which in turn rotates the staple former 2004, which in turn rotates the cartridge retainer 2010 and the staple cartridge 2001. The staple cartridge retainer 2010 is rotatably connected to a forward clevis 2011 of a clevis assembly 2011/2012 via channeled clam shell members 2009 which are captured by a sleeve 2000. These clam shell members 2009 rotate about an annular flange 2011a of the forward clevis 2011. The clevis member 2011/2012 does not, however, rotate upon rotation of the rod 2028.

The flexible member 2029 is flexible enough to allow the staple cartridge 2001 to be articulated, via the clevis 2011/2012, about an axis of articulation, A2, yet stiff enough to allow the staple driver rod 2028 to drive the staple former 2004, at any angle of articulation. The flexible attachment member 2029 is also capable of transferring torque from, and initiated at, the external knob 2040 to the rotatable staple cartridge 2001. Preferably, the flexible member 2029 comprises flexible cable, including wire, rod, chain, flex shaft, and true multi-strand cable. This flexible cable may be fabricated of any suitable material, including by way of example, but not limitation, steel, nitinol, nylon, and fiberglass. The flexible cable 2029 is preferably secured within the rod 2028 at its distal end 2028c, for example, by adhering the cable 2029 within a blind hole in the rod 2028 as previously described. The embodiment of FIGS. 51 and 52 offers significant advantages over previously described embodiments, in the that it allows one component, the rod 2028 and associated components to function as both a torque transfer mechanism, i.e. for rotating the staple cartridge 2001, as well as a staple driver device.

In a highly preferred embodiment of the invention, the flexible attachment member 2029 is slideably positioned within a flexible conduit attached to the instrument, e.g., at the clevis 2011 and/or 2012. This flexible conduit may be fabricated from any acceptable conduit material, including by way of example, but not limitation, woven, braided, bowden, extruded, and braided/extruded conduit. The flexible conduit is highly desireable, because it provides support to the flexible attachment member 2029, especially when that member has been bent into an angle of articulation by the clevis 2011/2012 as will subsequently be described.

The preferred embodiment of FIGS. 51, 51a, and 52 also includes a mechanism for articulating the staple cartridge 2001 about an axis of articulation A2. This mechanism preferably includes devices for providing pushing and/or pulling forces in a direction generally parallel to the support shaft 2026 and for directing those forces around the clevis 2011/2012 for pivoting the staple cartridge 2001 about the axis of articulation A2. In the embodiment illustrated in FIG. 51, this mechanism includes one or more articulation driver rods 2014, which are slideably positioned within the support shaft 2026 and spaced from the torque transfer/staple driver rod 2028. This spacing may be maintained, for example, by use of a spacer member 2027 having a series of spaced holes and/or grooves therein for maintaining a spaced orientation of the respective rods 2028 and 2014.

Most preferably, the articulation driver assembly includes a rigid section comprising a rigid rod 2014 having at its distal end a flexible section 2015, which flexible section provides both sufficient flexibility for bending about the axis of articulation, A2, while providing sufficient stiffness for transferring pushing forces around the clevis 2011/2012 without buckling. This flexible member 2015 may comprise a flexible cable similar to that previously discussed with respect to the flexible member 2029. This flexible member 2015 may also be attached to the articulation driver rod 2014 as previously described with respect to flexible member 2029.

Depending on whether a push/pull, push/push, or pull/pull arrangement is desired, the flexible members 2015 are attached to the staple cartridge 2001 in a number of ways, such as was previously described with respect to the embodiment illustrated in FIGS. 44-47.

As previously described with respect to FIGS. 44-47, the embodiment of FIGS. 51, 51a, and 52 also includes a control mechanism for transferring motion to the articulation driver assembly in a longitudinal direction generally parallel to the longitudinal axis, A1, of the support shaft 2026. This control apparatus preferably includes a control knob 2020 rotatably mounted on the support shaft, for example, with an axle 2021 and a mounting bracket 2024. The axle 2021 preferably includes a worm 2022 placed between washers 2023 that drives a worm gear 2019 that is attached via one or more pins 2018 to a sleeve 2017 which rides within an outer sleeve 2016 that is pinned to the sleeve 2017. The sleeve 2017 preferably comprises two halves 2017a and 2017b, each half having an inclined edge forming an inclined annular channel such as 706 previously described with respect to FIG. 44. The sleeves 2017 and 2016 may be housed within a cover 2025.

The annular channel in the sleeves 2017 captures flanges, which may comprise J-hooked ends 2014a of the articulation driver rods 2014, which ends extend through one or more longitudinal slots 2026a in the support shaft 2026. These flanges 2014a therefore slideably ride within the slots 2026a and are each driven along that slot(s) by the sleeve 2017 as that sleeve is rotated.

As discussed previously with respect to the embodiment of FIG. 44, it is preferred to include two or more articulation driver members 2014/2015 for articulating the staple cartridge 2001 about the clevis 2011/2012. As illustrated in FIG. 51, the rearward clevis 2012 preferably includes one or more grooves or slots 2012a having a thickness slightly greater than that of the cable 2015, which slides within and is guided by, the groove or slot 2012a. As also illustrated in FIG. 51, the clevis includes one or more pins 2013 which function to pivot the clevis about its pivot point, which corresponds to the axis A2 of articulation.

Referring now to FIGS. 53-58, there is illustrated in greater detail the clevis member 2011/2012. As illustrated in FIG. 53(a) the rear or stationary clevis 2012 includes an annular flange 2101 which is secured within the support tube 2026. This annular flange 2101 includes a number of bored holes 2102, 2103, 2104. As best seen in FIG. 57, the bored holes 2102 and 2104 slideably receive the flexible members 2015 and the bored hole 2103 slideably receives the flexible member 2029. Each of these flexible members in turn passes through the slot 2012(a) as previously described. The stationary clevis 2012 further includes a pair of planar flanges 2105, 2106, which define the slot 2012(a). Each flange 2105 and 2106 has a hole 2107, 2108 respectively, therethrough, for receiving the pins 2013 as previously described. The pins 2013 do not, however, penetrate the slot 2012(a).

Referring now to FIG. 54, there is illustrated the forward or moveable clevis, 2011, which includes an annular flange 2110 having a set of bored holes 2112, 2113, 2114 for receiving the respective flexible members from their counterpart bored holes 2102, 2103, 2104, respectively in the stationary clevis 2012. Preferably, the bored holes 2112 and 2114 are "blind" holes, in which the flexible members 2015 may be secured, for example, by an adhesive or crimping. The moveable clevis 2011 also includes a pair of planar flanges 2115, 2116, each of which includes a bored hole 2117, 2118 respectively, for receiving the pins 2013. The flanges 2115 and 2116 are separated by a space 2120, which is wide enough to accept the flanges 2105, 2106 of the stationary clevis 2012 as illustrated in FIG. 56.

In a highly preferred embodiment of the invention, the drivers 2014 operate in a push/pull mode, wherein as one driver 2014 is pushing the staple cartridge 2001 such that it articulates about the axis, A2, via the clevis 2011/2012, the other driver 2014 is pulling from the opposite side of the staple cartridge 2001. This is preferably achieved by affixing the cables 2015 to the forward clevis 2011, for example, by securing each of the cables 2015 within a blind hole, 2120 in the clevis 2011, as illustrated in FIGS. 57, 58. The forward clevis 2011 is attached via the cartridge retainer 2010 to the staple cartridge 2001, with each cable being placed on the center line, i.e., diameter, of the clevis 2011 and spaced apart from the axis, A1, of the cartridge and the clevis 2011 and on opposite sides of the center line with respect to that axis, as illustrated in FIGS. 52 and 54(c).

FIG. 55 illustrates the articulation of the embodiment of FIGS. 51 and 52. As illustrated, as the lower articulation driver rod 2014 is pushed in the direction of the arrow "A", and the upper articulation driver rod 2014 is pulled in the direction of the arrow "B", the moveable clevis 2011 is rotated about the pivot point, pin 2013, in the direction of arrow "C". This, in turn, articulates the staple cartridge 2001, which is fastened via the cartridge retainer 2010 to the moveable clevis 2011 as previously described.

Of course, it would be possible to impart a "push/push" and/or "push/push" mode of operation to the instrument, for example, by maintaining both cables 2015 in equal compression or tension, and providing means to vary the relative compression or tension, thereby inducing a net force for articulating the cartridge 2001. In the "pull/pull" mode, for example, both articulation driver rods 2014 would be biased forwardly, placing each of the flexible members 2015 in equal compression. A device for placing the biasing forces acting on the two rods 2014 in imbalance, such as a hand lever or toggle, would be used to cause a net force for articulating the cartridge in the direction of the net force. A similar arrangement would be used for the "pull/pull" mode, except that both rods 2014 would be biased rearwardly, such that the flexible members 2015 were in equal tension.

The invention in its broader aspects is not limited to the specific details of the preferred embodiments shown and described, and those skilled in the art will recognize that the invention can be practiced with modification within the spirit and scope of the appended claims, including any and all equivalents thereof. Additionally, although certain preferred embodiments of the invention described herein satisfy one or more objects and provide one or more advantages as discussed above, it is expressly contemplated that the invention may be practiced in spirit without utilizing all of the objects and advantages, and that accordingly, the objects and advantages of the invention form no part thereof, except as such may be embodied by the full scope of the following claims.

We claim:

1. A surgical stapling instrument for applying one or more surgical staples to tissue, said instrument comprising:

a support shaft having a longitudinal axis;

a staple cartridge containing a plurality of staples and mounted on said support shaft for pivotal movement about a transverse axis of articulation perpendicular to said shaft longitudinal axis to at least one articulated position, said cartridge containing a staple advancing and forming mechanism for effecting application of one of said staples to said tissue, said cartridge also being rotatable relative to said shaft about a cartridge axis defined along the length of said cartridge;

an operating rod generally traversing the length of said shaft longitudinal axis extending along said support shaft to said cartridge and connected with said staple advancing and forming mechanism, said rod including a flexible portion adjacent said transverse axis to accommodate the articulation of said instrument;

a knob connected to said rod proximally of said cartridge to rotate said cartridge relative to said shaft; and a staple actuator mechanism connected to said rod and operable from a location proximally of said cartridge to move said rod longitudinally for actuating said staple advancing and forming mechanism in said cartridge and to accommodate the rotation of said cartridge relative to said shaft;

wherein each said staple has a generally U-shaped body including a crown with a central offset portion between two non-offset portions and a pair of legs at opposite ends of said crown each depending from one of said non-offset portion; and said staple cartridge includes a staple storage region defined by a guide surface for supporting and guiding said staple crowns and includes a cavity for receiving said staple legs, said staples being arranged in a side-by-side stack in said storage region with each staple oriented transversely to the cartridge axis with the staple legs oriented perpendicularly to the cartridge axis;

a staple feeder shoe in said storage region and a spring biasing said feeder shoe distally along the length of said cartridge to engage the most proximal staple in said stack and urge said stack distally;

an inclined surface and an inclined ramp spaced from said inclined surface for receiving therebetween the distalmost staple from the stack at the distal end of said guide surface, said inclined surface and ramp each being oriented at an oblique angle relative to said cartridge axis; and spaced-apart extension surfaces for receiving said staple crown as said staple advances distally from said inclined surface and inclined ramp whereby said non-offset portions engage said ramp to rotate said staple about 90° into an orientation with the staple legs oriented parallel to said cartridge axis and pointing toward the distal end of said cartridge.

2. The instrument in accordance with claim 1 in which said rod includes a rigid portion in said support shaft and that includes said flexible portion extending from said rigid portion.

3. The instrument in accordance with claim 2 in which said staple advancing and forming mechanism is connected to the distal end of said rod flexible portion;

said instrument includes a handle from which said support shaft extends;

said staple actuator mechanism includes a trigger on said handle operatively engaged with said rod for effecting longitudinal movement thereof to drive said staple advancing and forming mechanism to advance and form one of said staples; and said knob is rotatably mounted on said handle and engaged with said rod to effect rotation of said rod relative to said shaft to rotate said cartridge about said cartridge axis.

4. The stapling instrument in accordance with claim 1 in which said instrument includes a pivot connection structure connecting said staple cartridge to said support shaft for accommodating the pivotal movement of said staple cartridge about said transverse axis;

said pivot connection structure includes a pivotable member that is pivotable relative to said support shaft;

said staple cartridge is mounted to said pivotable member for rotation about said cartridge axis; and said instrument includes an articulation driver operable from a location proximally of said pivotable member for pivoting said member.

5. The stapling instrument in accordance with claim 4 in which said staple cartridge includes a hollowing cartridge housing containing said staple advancing and forming mechanism operatively connected to said rod, said staple advancing and forming mechanism including a former that is longitudinally reciprocable within said hollow cartridge housing; and said former has a proximal end for engaging said rod to accommodate rotation of said former with said cartridge about the cartridge axis relative to said support shaft.

6. The staple instrument in accordance with claim 5 in which said instrument further includes a retainer having (A) a proximal end mounted to said pivotable member to accommodate rotation of said retainer relative to said pivotable member; and (B) a distal end received in said hollow cartridge housing for rotation of said retainer.

7. The instrument in accordance with claim 1 in which said instrument includes a pivotable member at the distal end of said support shaft for mounting said staple cartridge for pivotal movement relative to said support shaft about said transverse axis;

an articulation driver operable from a location proximally of said cartridge to pivot said staple cartridge relative to said support shaft, said articulation driver including at its distal end one of a guide pin and arcuate groove, said pivotable member including the other of said guide pin and arcuate groove, said guide pin being received in said arcuate groove for converting the longitudinal movement of said articulation driver into pivotal movement of said pivotable member and staple cartridge mounted thereon relative to said support shaft.

8. A surgical stapling instrument for applying one or more surgical staples to tissue, said instrument comprising:

a support shaft having a longitudinal axis;

a staple cartridge containing a plurality of staples and mounted on said support shaft for pivotal movement about a transverse axis of articulation perpendicular to said shaft longitudinal axis to at least one articulated position, said cartridge containing a staple advancing and forming mechanism for effecting application of one of said staples to said tissue, said cartridge also being rotatable relative to said shaft about a cartridge axis defined along the length of said cartridge;

an operating rod generally traversing the length of said shaft longitudinal axis extending along said support shaft to said cartridge and connected with said staple advancing and forming mechanism, said rod including a flexible portion adjacent said transverse axis to accommodate the articulation of said instrument;

a knob connected to said rod proximally of said cartridge to rotate said cartridge relative to said shaft; and a staple actuator mechanism connected to said rod and operable from a location proximally of said cartridge to move said rod longitudinally for actuating said staple advancing and forming mechanism in said cartridge and to accommodate the rotation of said cartridge relative to said shaft;

wherein each said staple has (A) a generally U-shaped body including a crown, and
(B) a pair of legs each depending from opposite end of said crown;

said staples are arranged in a side-by-side stack oriented transversely to the cartridge axis with the staple legs oriented perpendicularly to the cartridge axis; and said staple advancing and forming mechanism engages the distalmost staple to advance the distalmost staple distally to effect engagement of part of said staple crown with a part of said cartridge whereby the staple rotates about ninety degrees to an orientation with the staple legs oriented parallel to the cartridge axis.

* * * * *